US011535858B2

(12) United States Patent
Botto et al.

(10) Patent No.: US 11,535,858 B2
(45) Date of Patent: Dec. 27, 2022

(54) POLYNUCLEOTIDE CONSTRUCT FOR IMPROVING AGRICULTURAL CHARACTERISTICS IN CROP PLANTS

(71) Applicants: CONSEJO NACIONAL DE INVESTIGACIONES CIENTÍFICAS Y TÉCNICAS (CONICET), Ciudad Autónoma de Buenos Aires (AR); UNIVERSIDAD DE BUENOS AIRES, Ciudad Autónoma de Buenos Aires (AR)

(72) Inventors: Javier Francisco Botto, Martínez (AR); Carlos Daniel Crocco, Escobar (AR)

(73) Assignees: CONSEJO NACIONAL DE INVESTIGACIONES CIENTÍFICAS Y TÉCNICAS (CONICET), Ciudad Autónoma de Buenos Aires (AR); UNIVERSIDAD DE BUENOS AIRES, Ciudad Autónoma de Buenos Aires (AR)

( * ) Notice: Subject to any disclaimer, the term of this patent is extended or adjusted under 35 U.S.C. 154(b) by 0 days.

(21) Appl. No.: 16/818,226

(22) Filed: Mar. 13, 2020

(65) Prior Publication Data
US 2020/0299711 A1   Sep. 24, 2020

Related U.S. Application Data

(60) Provisional application No. 62/819,919, filed on Mar. 18, 2019.

(51) Int. Cl.
*C12N 15/82*   (2006.01)
*C07K 14/415*   (2006.01)

(52) U.S. Cl.
CPC ........ *C12N 15/8261* (2013.01); *C07K 14/415* (2013.01)

(58) Field of Classification Search
CPC .......................... C12N 15/8261; C07K 14/415
See application file for complete search history.

(56) References Cited

U.S. PATENT DOCUMENTS

2007/0039067 A1* 2/2007 Feldmann ............ C07K 14/415
800/278

OTHER PUBLICATIONS

Carlos D. Crocco, Magnus Holm, Marcelo J. Yanovsky and Javier F. Botto, "AtBBX21 and COP1 genetically interact in the regulation of shade avoidance," The Plant Journal (2010) 64, 551-562 (Year: 2010).*

(Continued)

*Primary Examiner* — Matthew R Keogh
*Assistant Examiner* — David R Byrnes
(74) *Attorney, Agent, or Firm* — Muncy, Geissler, Olds & Lowe, P.C.

(57) ABSTRACT

The present invention generally relates to the field of genetic engineering and obtaining transgenic traits for agronomic applications. More specifically, the present invention relates to a specific transgenic event in agricultural crops that improves plant characteristics. Yet more specifically, the invention relates to a polynucleotide construct comprising a gene from *Arabidopsis thaliana*. In particular, the polynucleotide construct of the invention comprises the gene AtBBX21 which encodes a B-box protein from *Arabidopsis thaliana*. The transgenic event of the invention increases green and seed yield, reduces photoinhibition, improves water use efficiency, increases tuber and chlorophyll production and improves photosynthetic rates, among others. The polynucleotide construct of the invention comprises a sequence depicted as SEQ ID NO: 1. The invention also provides a transgenic plant transformed with said polynucleotide construct, wherein said plant exhibits improved characteristics. In a particularly preferred embodiment, the transgenic plant is a potato (*Solanum tuberosum*) plant that (Continued)

overexpresses a gene from *Arabidopsis thaliana*, wherein said potato plant exhibits improved characteristics.

6 Claims, 18 Drawing Sheets

Specification includes a Sequence Listing.

(56) References Cited

OTHER PUBLICATIONS

Carlos D. Crocco, Gabriel Gomez Ocampo, Edmundo L. Ploschuk, Anita Mantese and Javier F. Botto; "Heterologous Expression of AtBBX21 Enhances the Rate of Photosynthesis and Alleviates Photoinhibition in Solanum tuberosum." Plant Physiology (2018) vol. 177, Issue 1 (Year: 2018).*

Crocco et al., "Heterologous Expression of AtBBX21 Enhances the Rate of Photosynthesis and Alleviates Photoinhibition in *Solanum tuberosum*," Plant Physiology, May 2018, vol. 177, pp. 1-12, 12 pages.

* cited by examiner

BBX21 cloned from cDNA
(Job, et al. 2018)
BBX21 cloned from DNA
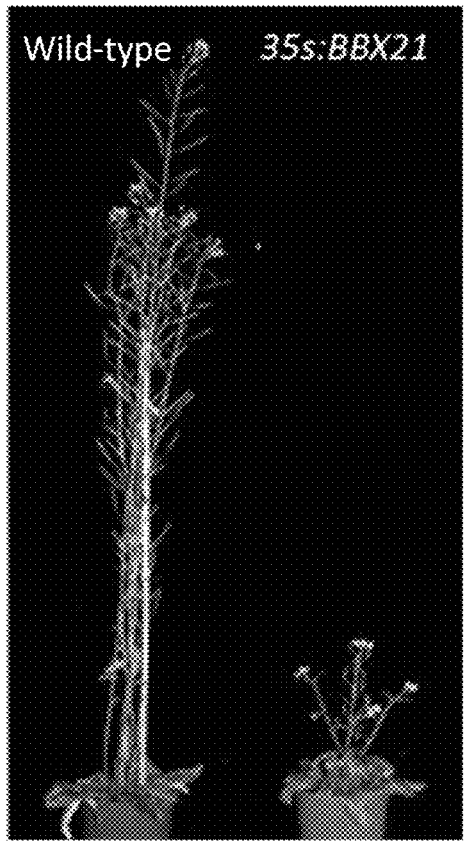
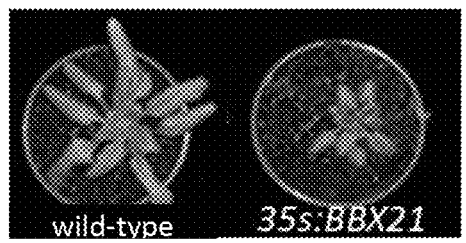
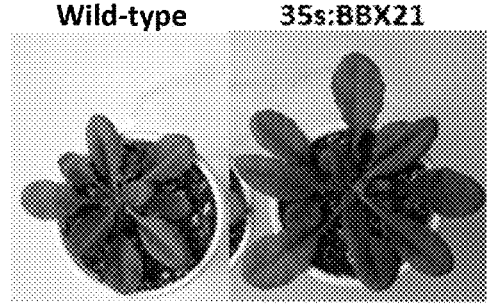
Fig. 2A
Fig. 2B

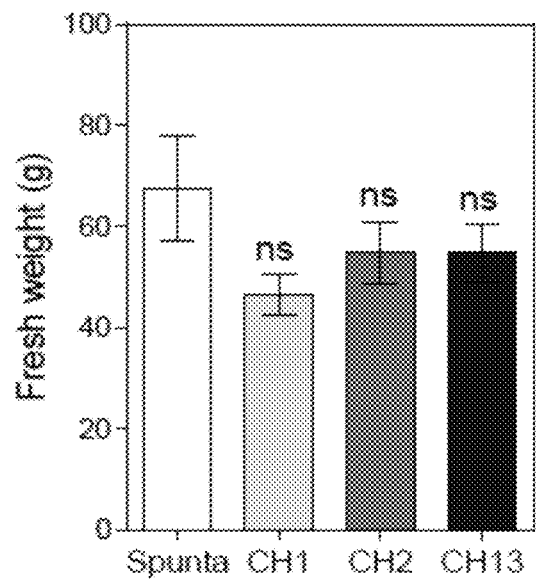
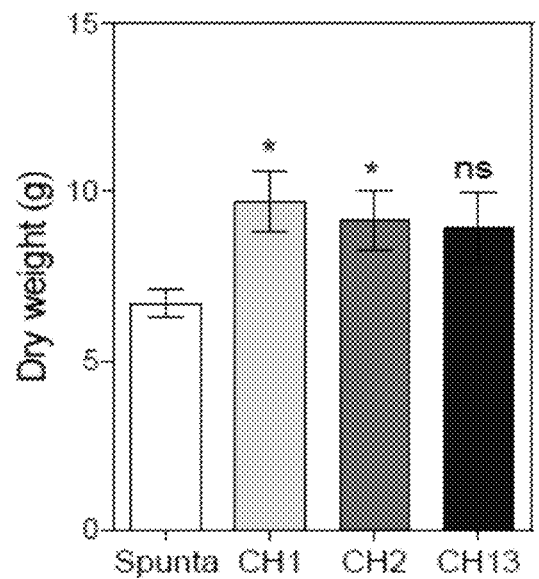
Fig. 6A          Fig. 6B
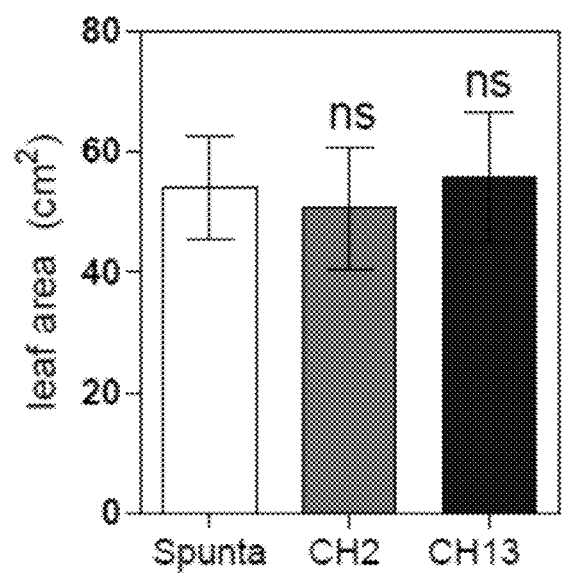
Fig. 7

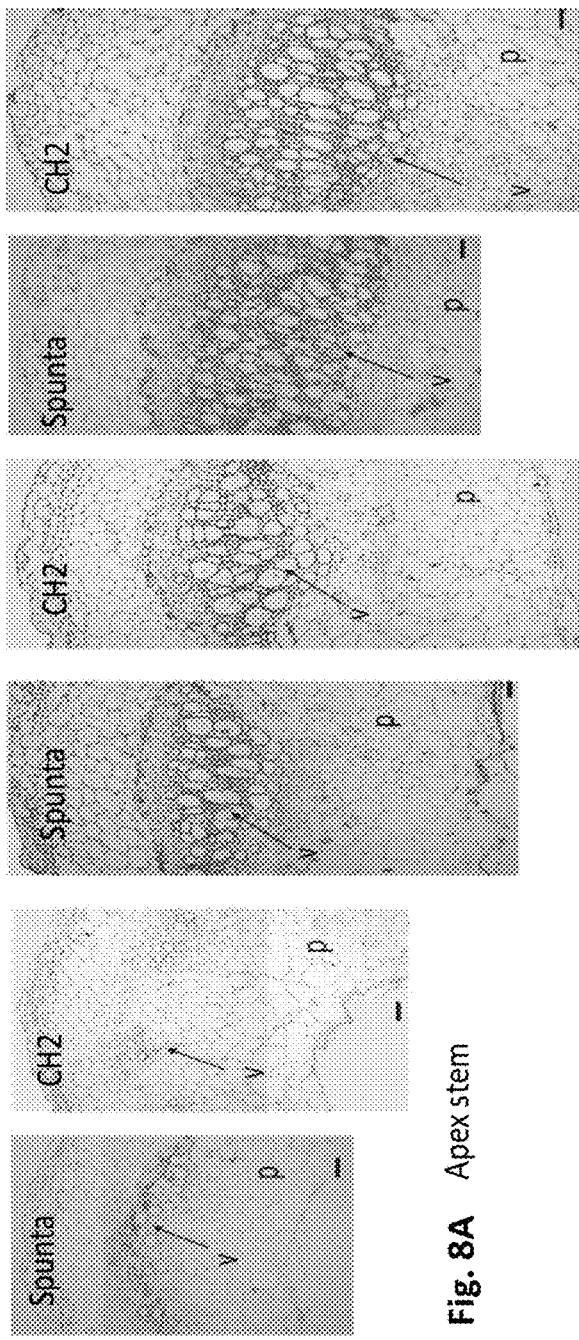
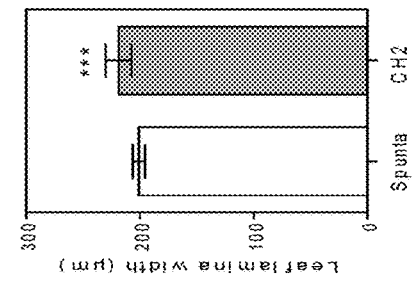
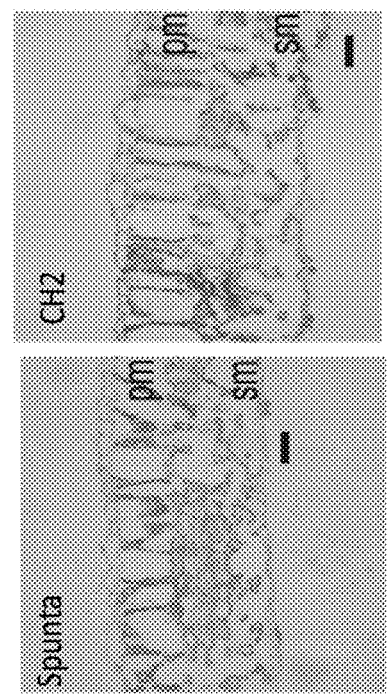
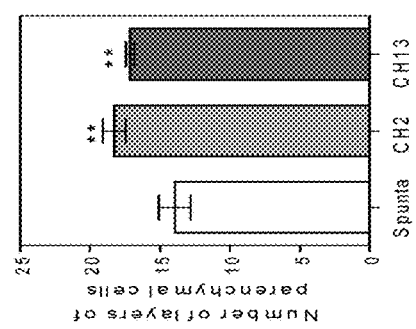
Fig. 8A Apex stem
Fig. 8B Middle stem
Fig. 8C Basal stem
Fig. 8D
Fig. 8E
Fig. 8F

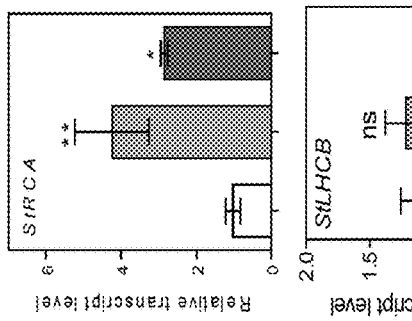
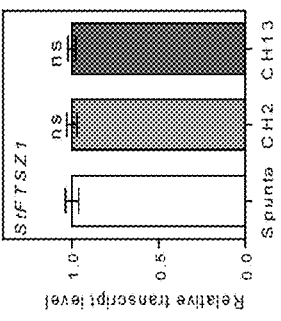
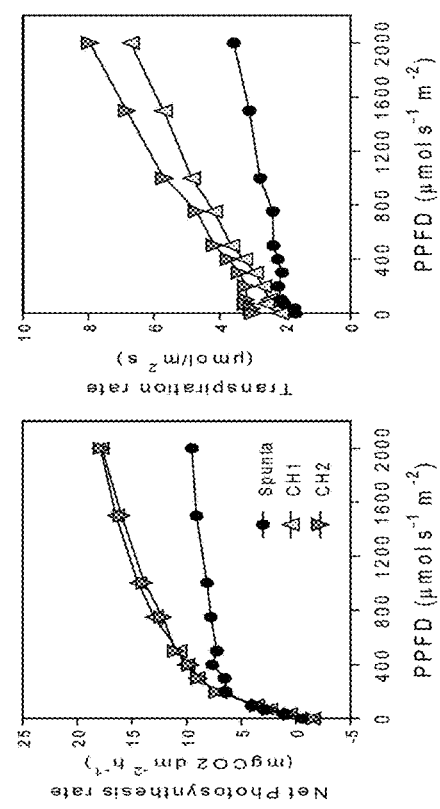
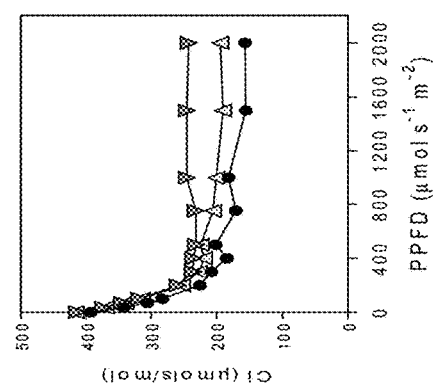
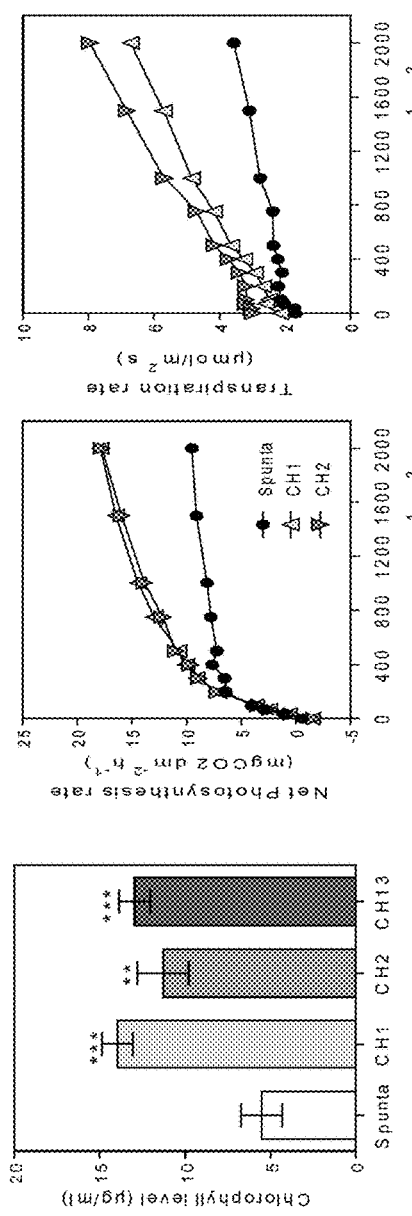
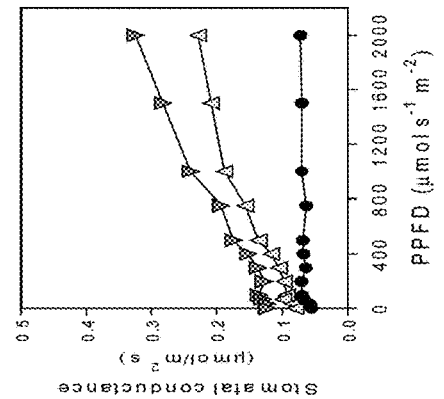
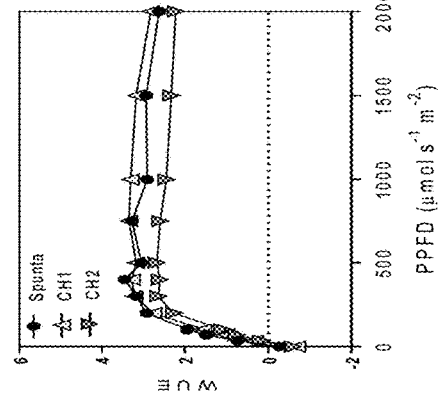

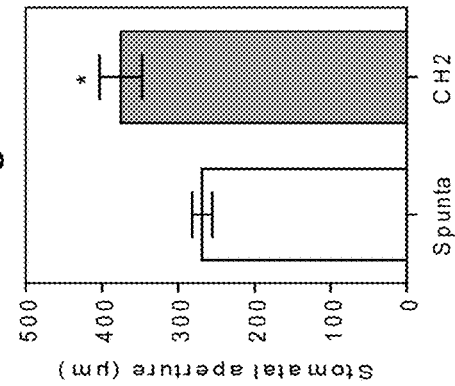
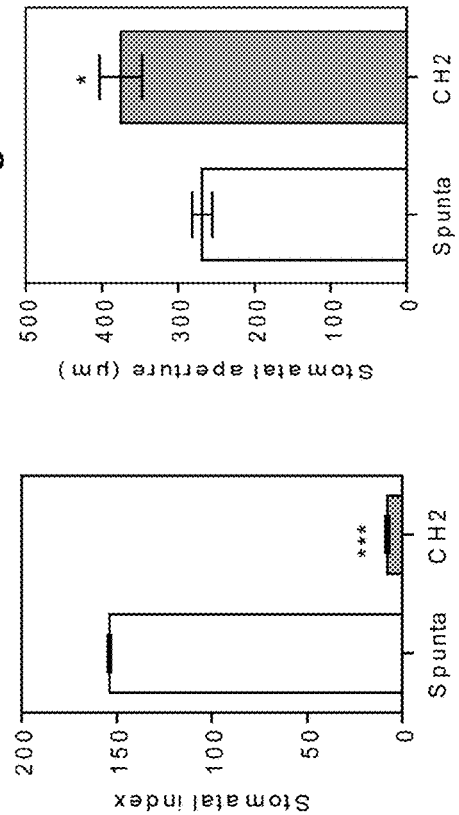
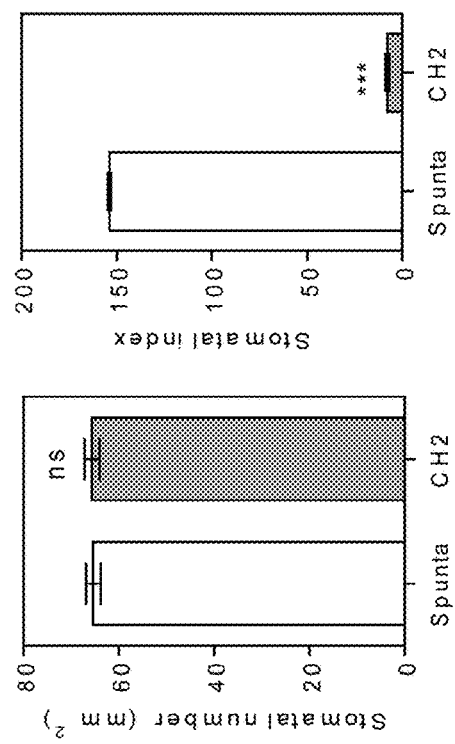
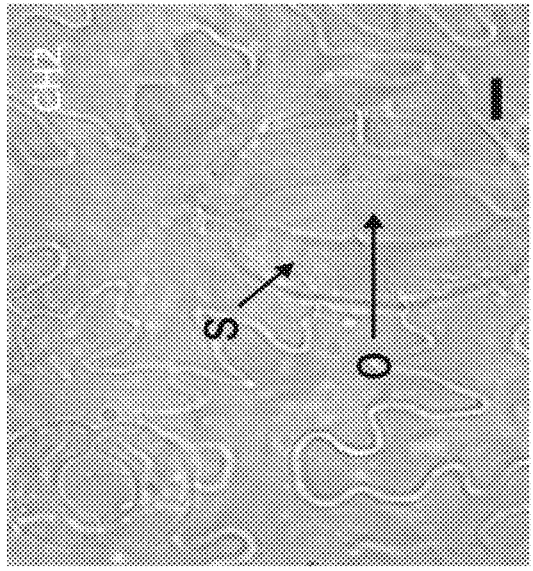
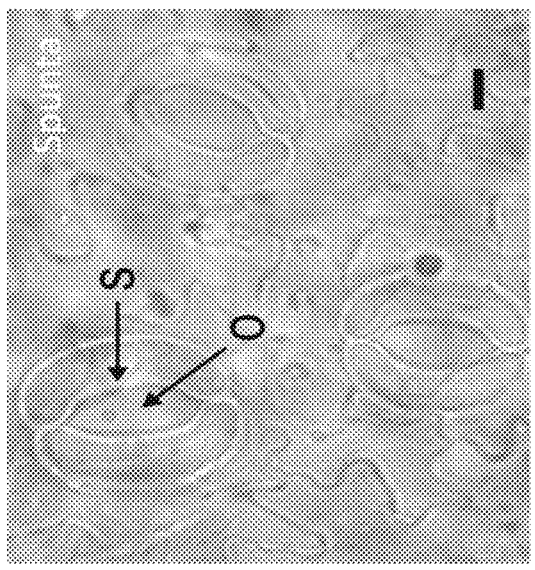
Fig. 11A  Fig. 11B  Fig. 11C  Fig. 11D

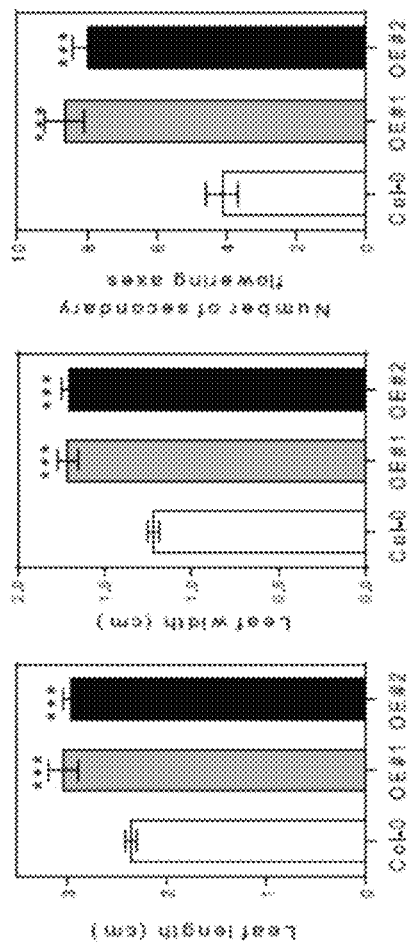
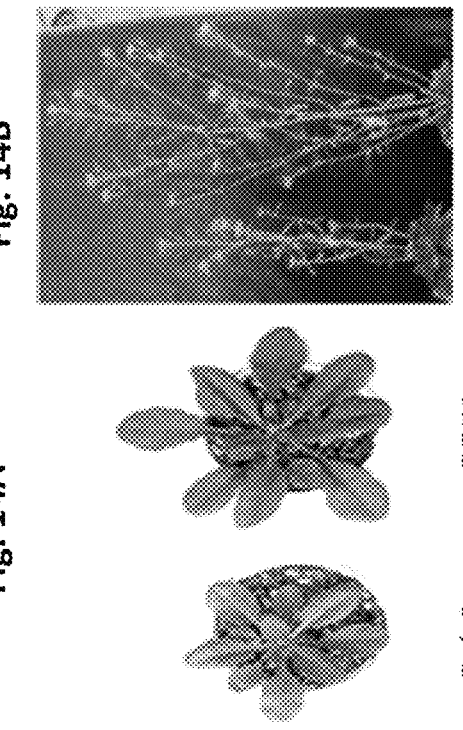
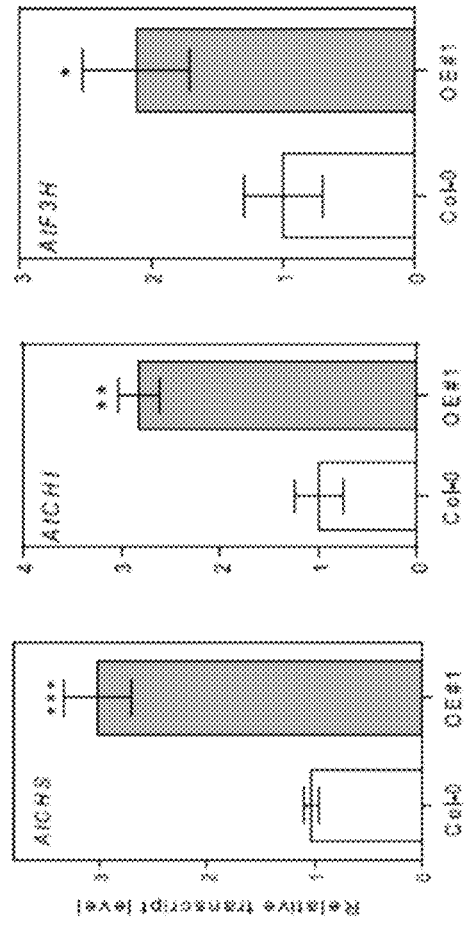
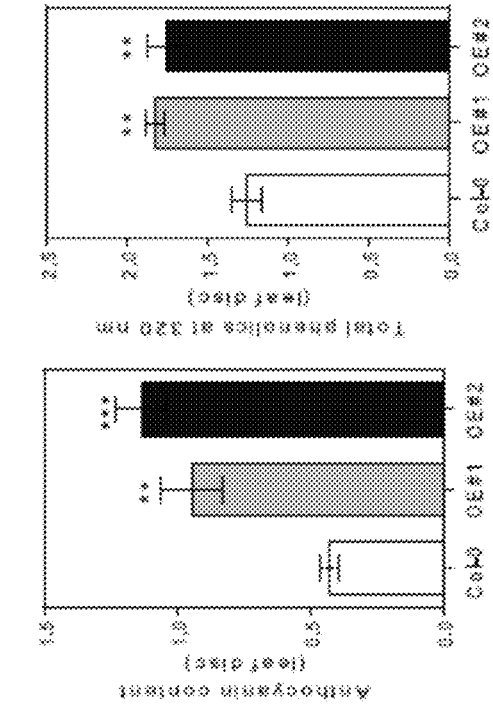

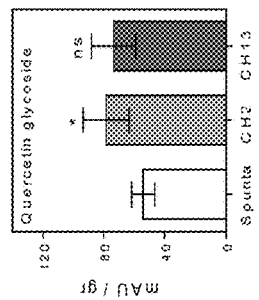
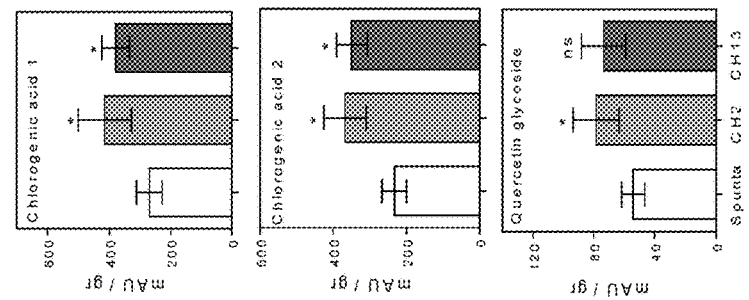
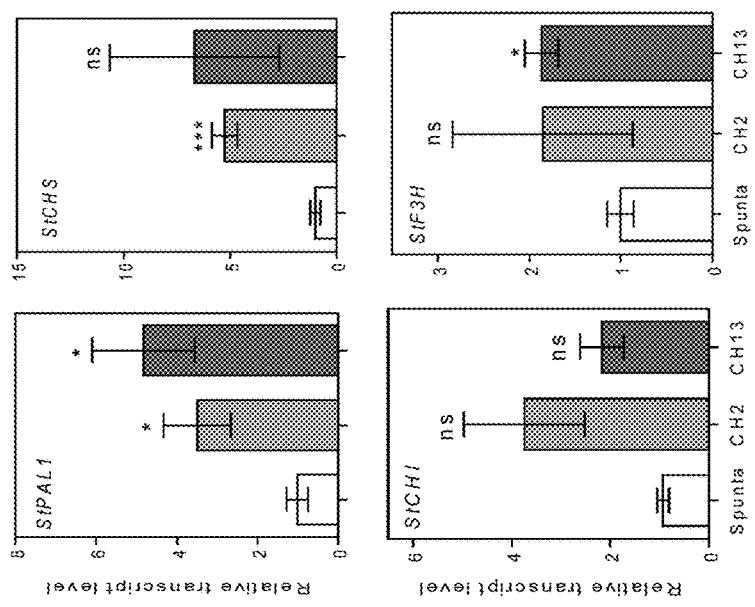
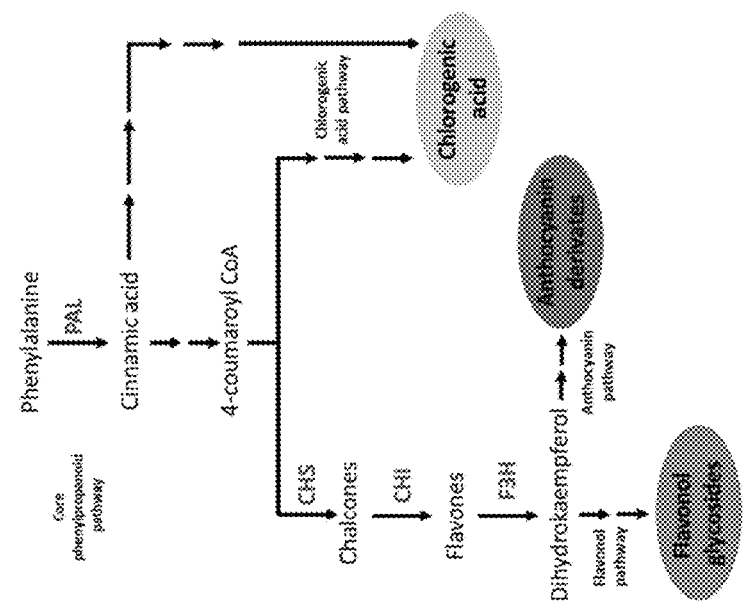

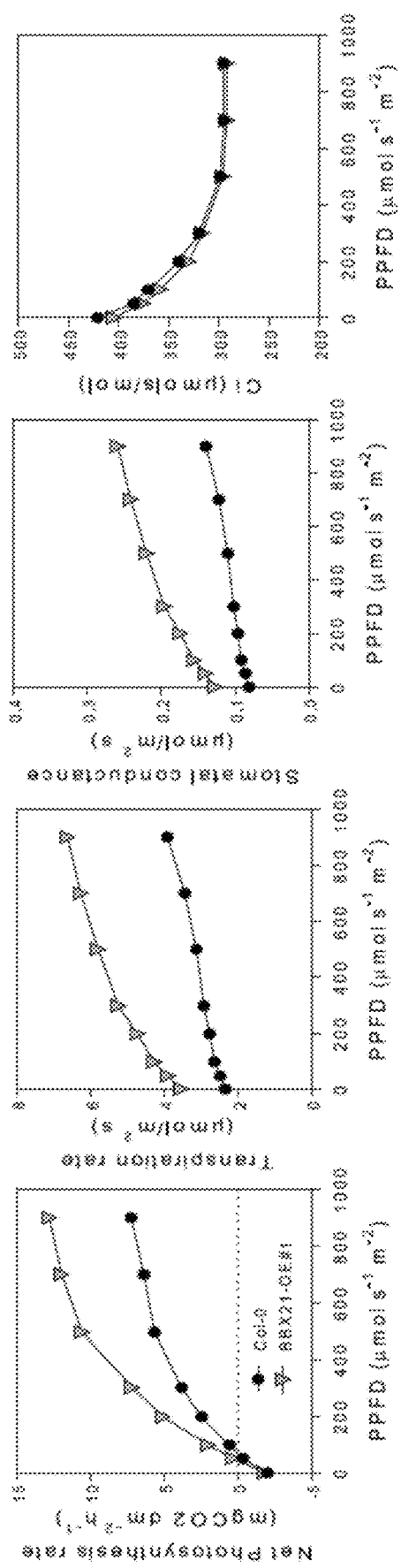
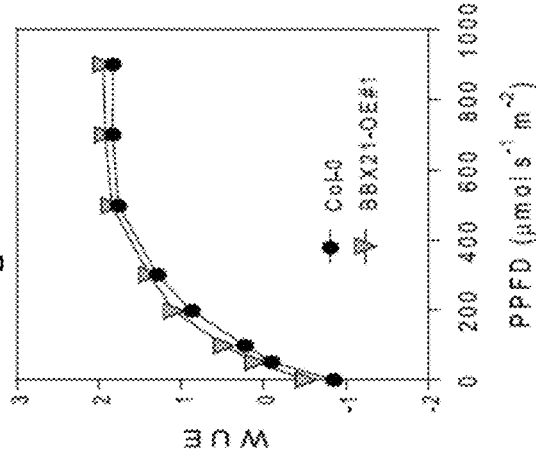

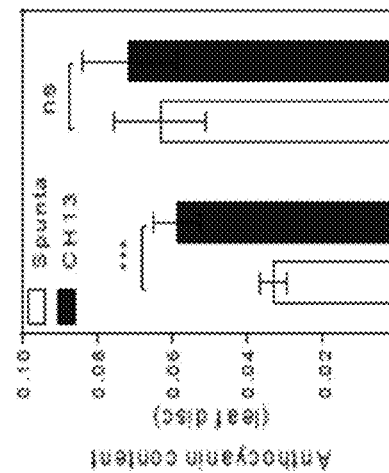
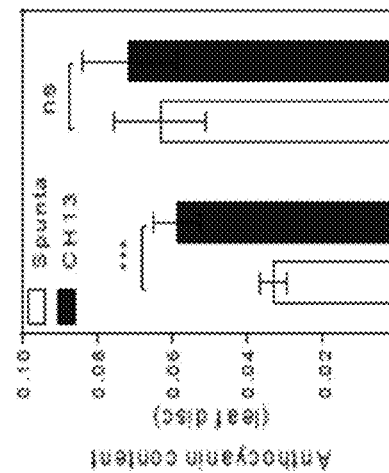
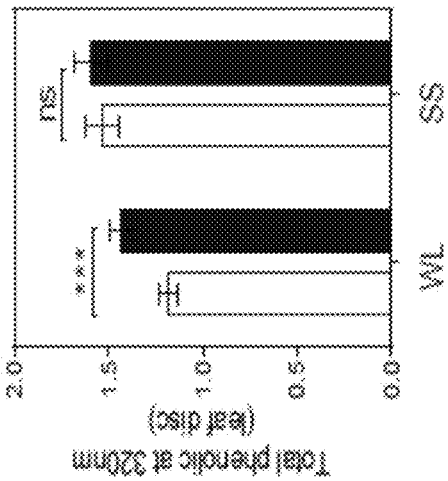
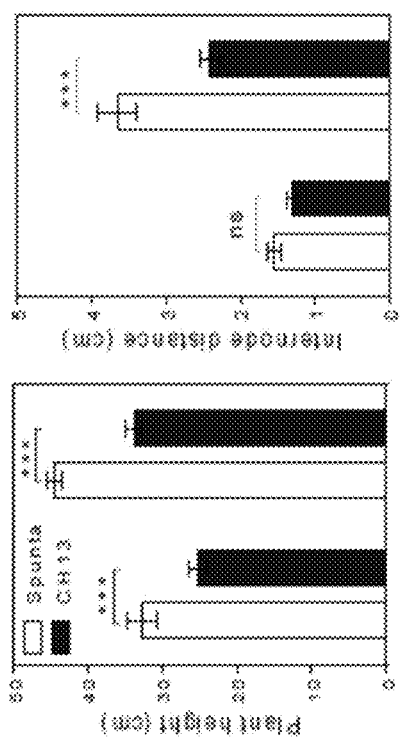
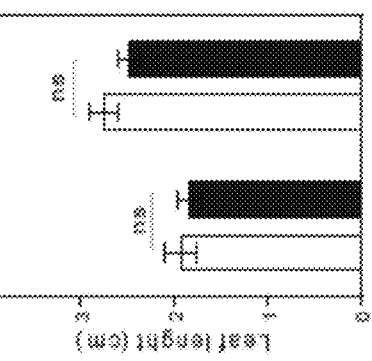
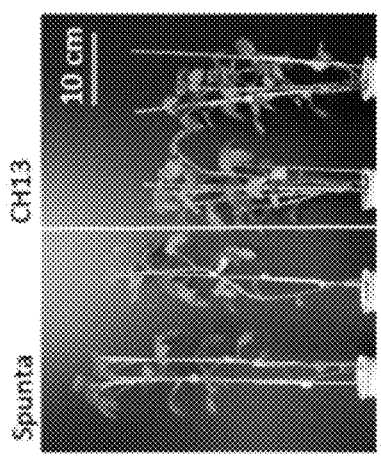
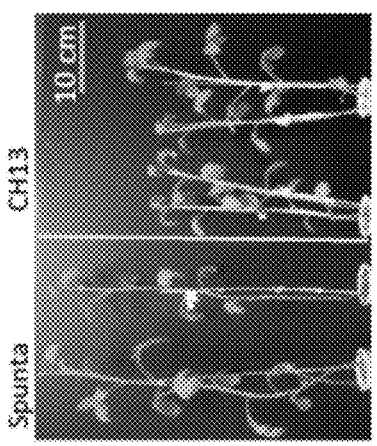
Fig. 17A, Fig. 17B, Fig. 17C, Fig. 17D, Fig. 17E, Fig. 17F, Fig. 17G, Fig. 17H

POLYNUCLEOTIDE CONSTRUCT FOR IMPROVING AGRICULTURAL CHARACTERISTICS IN CROP PLANTS

CROSS REFERENCE TO RELATED APPLICATIONS

This application claims priority of U.S. Provisional Application No. 62/819,919 filed on Mar. 18, 2019 under 35 U.S.C. § 119(e), the entire contents of all of which are hereby incorporated by reference.

FIELD OF THE INVENTION

The present invention generally relates to the field of genetic engineering and obtaining transgenic traits for agronomic applications. More specifically, the present invention relates to a specific transgenic event in agricultural crops that improves plant characteristics. Yet more specifically, the invention relates to a polynucleotide construct comprising a gene from *Arabidopsis thaliana*. In particular, the polynucleotide construct of the invention comprises the gene AtBBX21 which encodes a B-box protein from *Arabidopsis thaliana*. The transgenic event of the invention increases green and seed yield, reduces photoinhibition, improves water use efficiency, increases tuber and chlorophyll production and improves photosynthetic rates, among others. The polynucleotide construct of the invention comprises a sequence depicted as SEQ ID NO: 1. The invention also provides a transgenic plant transformed with said polynucleotide construct, wherein said plant exhibits improved characteristics. In a particularly preferred embodiment, the transgenic plant is a potato (*Solanum tuberosum*) plant that overexpresses a gene from *Arabidopsis thaliana*, wherein said potato plant exhibits improved characteristics.

BACKGROUND OF THE INVENTION

Sunlight is essential for autotrophic life. Radiation intensity (measured as photosynthetic photon flux density [PPFD]) is a determinant of plant photosynthesis, during which solar energy is converted into chemical energy and stored as organic carbon. The productivity of a crop depends not only on its photosynthetic rate, but also on other ecophysiological parameters related to crop architecture, such as intercepted radiation and radiation use efficiency (Sinclair T R, Muchow R C (1999) *Radiation use efficiency*. Adv Agron 65: 215-265; Monteith J L, Moss C J (1977) *Climate and the efficiency of crop production in Britain*. Philos Trans R Soc Lond B Biol Sci 281: 277-294).

Light also serves as a sensory cue for the adjustment of plant architecture (Casal J J (2013) *Photoreceptor signaling networks in plant responses to shade*. Annu Rev Plant Biol 64: 403-427). Molecular genetic studies of model plants in the past few decades have identified many key genes and pathways that control plant photomorphogenesis. Light absorption by different photoreceptors leads to modulation of core signaling networks, which further orchestrates specific hormone and metabolic signaling pathways to precisely affect growth and development (Quail P H (2002) *Photosensory perception and signalling in plant cells: new paradigms*? Curr Opin Cell Biol 14: 180-188; Lau O S, Deng X W (2012) *The photomorphogenic repressors COP1 and DET1: 20 years later*. Trends Plant Sci 17: 584-593). Photoreceptors activate many intermediary transcription factors that belong to diverse families that bind to light responsive elements to activate or repress transcription.

During the hours of the day when the highest levels of solar radiation occur, field-grown plants may experience a process known as photoinhibition. This process is defined as the inhibition of photosynthesis caused by an excess of light, causing a situation of stress in the plants that ultimately affects the daily production of photoassimilates and consequently the final yield of the crops. The effects of light stress are so detrimental to yields that diffusing structures are normally used in many intensive crops to distribute incident sunlight to reduce the stress associated with excess light and allow higher yields of plants grown under these structures. However, in extensive crops, which are carried out on larger areas, the use of diffusing structures is not a feasible practice. The generation of biotechnological events that allow modifying some aspects of the plants so that they can adapt to high solar radiation conditions can be a solution to this problem. The present invention is based on the genetic engineering of a gene that allows generation of improved phenotypes in the modified plants. Consequently, modified plants according to the invention behave better towards different stress conditions, thus displaying a higher yield than conventional plants, among other beneficial characteristics.

The transgenic events developed to date were focused on the overexpression of genes encoding photoreceptors. These genes are central regulators of plant development, which implies that their manipulation may affect many signaling pathways that can favor a physiological character and at the same time harm another. For example, *Solanum tuberosum* plants that overexpress the phytochrome B (PhyB) gene, one of the main photoreceptors, produce more robust plants with a higher content of anthocyanins and chloroplasts than non-transformed plants. Although the phenotype of overexpression of phyB improves some characteristics, it also affects other important parameters such as water use efficiency, which is not a positive effect. This means that phyB-overexpressing plants have a high transpiration rate that generates water stress in the plant and can affect the final yield thereof in the field. However, the event proposed herein surgically alters a signaling path that does not modify the efficiency in the use of water at least in optimal water conditions (Boccalandro H E (2003) *Increased phytochrome B alleviates density effects on tuber yield of field potato crops*. Plant Physiol 33:1539-46).

Several transcription factors, functioning downstream of one or multiple photoreceptors, have been functionally characterized. For example, ELONGATED HYPOCOTYL5 (HY5) is a central positive regulator of photomorphogenic development in *Arabidopsis* (*Arabidopsis thaliana*; Gangappa S N, Botto J F (2016) *The multifaceted roles of HY5 in plant growth and development*. Mol Plant 9: 1353-1365). HY5 genetically and physically interacts with many signaling components to promote or suppress photomorphogenesis. One important partner of HY5 is CONSTITUTIVE PHOTOMOPHOGENIC1 (COP1), a key suppressor of photomorphogenesis (Lau and Deng, op. cit.). COP1 targets HY5 and many other transcription factors for degradation under dark conditions to promote skotomorphogenesis.

B-box (BBX) proteins are zinc-finger transcription factors containing one or two B-box motifs. These B-box (BBX) transcription factors also interact physically or genetically with HY5 and COP1. The BBX proteins are a functionally diverse family encoded by genes that are highly conserved across all multicellular plants, including blue-green algae and mosses (Gangappa S N, Botto J F (2014) *The BBX family of plant transcription factors*. Trends Plant Sci 19: 460-470). In *Arabidopsis*, 21 out of the 32 BBX proteins (BBX1-13 and BBX18-25) contain two B-boxes in tandem, whereas 11 (BBX14-BBX17 and BBX26-BBX32) contain one B-box. BBX21 regulates plant growth and development throughout the life cycle. BBX21 promotes seed germination in an abscisic acid-dependent manner by interfering with HY5 binding to the ABA-INSENSITIVE5 (ABI5) promoter to inhibit ABI5 expression (Xu D, Li J, Gangappa S N, Hettiarachchi C, Lin F, Andersson M X, Jiang Y, Deng X W, Holm M (2014) *Convergence of Light and ABA signaling on the ABI5 promoter*. PLoS Genet 10: e1004197). In addition, BBX21 binds to the T/G-box in the HY5 promoter and directly activates HY5 expression in the light-promoting seedling photomorphogenesis (Xu D, Jiang Y, Li J, Lin F, Holm M, Deng XW (2016) *BBX21, an Arabidopsis B-box protein, directly activates HY5 and is targeted by COP1 for 26S proteasome-mediated degradation*. Proc Natl Acad Sci USA 113: 7655-7660). The disruption of the second B-box in BBX21 impairs its ability to bind to the HY5 promoter (Xu D, Jiang Y, Li J, Holm M, Deng X W (2018) *The B-box domain protein BBX21 promotes photomorphogenesis*. Plant Physiol 176: 2365-2375). The relevance of BBX21 to light and abscisic acid signaling in seedling development is well established; however, its importance in adult plant development and agronomic species is poorly understood. Interestingly, BBX32, a BBX that represses seedling photomorphogenesis, physically interacts with BBX21 leading to the inactivation of the BBX21-HY5 protein complex (Holtan H E, Bandong S, Marion C M, Adam L, Tiwari S, Shen Y, Maloof J N, Maszle D R, Ohto M A, Preuss S, et al (2011) *BBX32, an Arabidopsis B-Box protein, functions in light signaling by suppressing HY5-regulated gene expression and interacting with STH2/BBX21*. Plant Physiol 156: 2109-2123). Furthermore, BBX21 reduces hypocotyl growth in seedlings exposed to shade light by down-regulating cell growth genes through the COP1 signaling pathway (Crocco C D, Holm M, Yanovsky M J, Botto J F (2010) *AtBBX21 and COP1 genetically interact in the regulation of shade avoidance*. Plant J 64: 551-562).

The BBX proteins constitute a diverse group of transcription factors whose members have opposing functions; these functions contribute to the homeostatic integration of endogenous and environmental signals for the fine-tuning of several physiological processes (Gangappa S N, Botto J F (2014) op. cit.; Crocco C D, Locascio A, Escudero C M, Alabadi D, Blázquez MA, Botto J F (2015) *The transcriptional regulator BBX24 impairs DELLA activity to promote shade avoidance in Arabidopsis thaliana*. Nat Commun 6: 6202). It has also been suggested that BBX proteins mediate the adjustment of plant growth under stress (Gangappa S N, Botto J F (2014) op. cit.). The present inventors focused their research experimentation to further characterize the role of BBX21 in order to determine its function in adult plants with a view to obtaining desirable agronomic characteristics.

Over the last few years, many scientific publications have reported that manipulating the expression of B-Box genes encoding zinc finger proteins, both in *A. thaliana* and other species, might improve some interesting characteristics for agronomic application (Gangappa S N, Botto J F (2014) op. cit.). However, characterization of BBXs transgenic plants generated to date may be considered weak in the sense that only incomplete physiological parameters have been assessed, without a detailed evaluation of other important physiological and agronomic aspects, such as photosynthesis. As a result, it would be impossible to foresee whether overexpression of the characterized BBX genes would provide an improvement in plant yield without affecting other vital mechanisms and processes that may compromise the optimal functioning of the plant.

On the other side, the BBX genes overexpression events are evaluated on the model species of interest, and thus there is no information about generalities and relevance of the studied phenomena. In view of this, the present inventors have extensively investigated the overexpression of X21 construct in different species and have surprisingly demonstrated that the transgenic plants obtained are more robust, have higher photosynthetic rates and higher yield, due to a higher production of photoprotective pigments that allow the plant to better respond to photoinhibition of the system towards high irradiances in *Arabidopsis thaliana* and potato (*Solanum tuberosum*).

The approach to this issue and the complete characterization of the plant material obtained by the present inventors, is of high relevance because the molecular and biological functions of BBX regulators are diverse and the engineering thereof may provide an agronomic advantage at the expense of other physiological processes, which would make these projects unfeasible from a commercial point of view.

It should be mentioned that, another known transgenic event in soy plants has been disclosed in U.S. Pat. No. 9,493,786 B2 (Monsanto). According to this patent, expression of BBX32 gene from *Arabidopsis* in soy plants results in an increased yield (Preuss S B, Meister R, Xu Q, Urwin C P, Tripodi F A, Screen S E, Anil V S, Zhu S, Morrell J A, Liu G, et al (2012) *Expression of the Arabidopsis thaliana BBX32 gene in soybean increases grain yield*. PLoS One 7: e30717). However, it was observed by the present inventors that overexpression of such gene in *Arabidopsis* may produce smaller plants and with a lower yield than wild-type plants, as can be seen in the images of FIG. 1. These results, which are apparently contradictory, suggest that the claimed BBX32 event may not be a good alternative for vegetal enhancement programs for other plant species. BBX32 is a little conserved gene among the plant kingdom and its genetic structure is simple because it only contains one exon (Crocco C D, Botto J F (2013) *BBX proteins in green plants: insights into their evolution, structure, feature and functional diversification*. Gene 531: 44-52; Gangappa S N, Botto J F (2014) op. cit.). These might be the reasons why BBX32 overexpression has beneficial characteristics in soybean that cannot be extrapolated to other species, such as *Arabidopsis*.

As opposed to the BBX32 event mentioned above, the BBX21 gene is highly conserved among monocotyledonous and dicotyledonous plants, as well as in lower photosynthetic organisms (Crocco C D, Botto J F (2013) op. cit.). This structural conservation and the reproducibility of the advantageous features provided by the X21 event, as found herein by the present inventors in *Arabidopsis*, potato and other species of agronomical interest, allow for increasing the green and seed yield without affecting other relevant agronomical parameters, as previously reported (Crocco C D, Ocampo G G, Ploschuk E L, Mantese A, Botto J F (2018). *Heterologous Expression of AtBBX21 Enhances the Rate of Photosynthesis and Alleviates Photoinhibition in Solanum tuberosum*. Plant Physiol. 177:39-380).

Hence, by studying morphological, biochemical, physiological, and photosynthetic effects of the heterologous expression of AtBBX21 gene in potato (*Solanum tuberosum*) var Spunta and *Arabidopsis* the inventors were able to design crop varieties having enhanced agronomic features, without negatively affecting other characteristics of agronomic importance such as water usage in the plant, thus, providing a solution to the prior art problem discussed above.

SUMMARY OF THE INVENTION

B-box (BBX) proteins are zinc-finger transcription factors containing one or two B-box motifs. BBX proteins act as key factors in the networks regulating growth and development. The relevance of BBX21 to light and abscisic acid signaling in seedling development is well established; however, its importance in adult plant development and agronomic species is poorly understood. Therefore, the effect of heterologous expression of *Arabidopsis* (*Arabidopsis thaliana*) BBX21 in potato (*Solanum tuberosum*) var Spunta was studied. Three independent AtBBX21-expressing lines and a wild-type control were cultivated under sunlight and at controlled temperatures in a greenhouse. By anatomical, physiological, biochemical, and gene expression analysis, the present inventors demonstrated that AtBBX21-expressing plants were more robust and produced more tubers than wild-type plants.

The present invention is based on the genetic engineering of a gene that allows attenuating the effects of photoinhibition in plants modified with the polynucleotide construct according to the invention, maintaining higher photosynthetic rates than non-transformed plants when grown under conditions of high irradiances. Consequently, the modified plants of the invention behave better towards the stress produced by light changes, thus generating a higher yield than conventional plants.

In other words, AtBBX21-expressing plants as disclosed herein had higher rates of photosynthesis, with a significant increase in photosynthetic gene expression, and higher stomatal conductance, with increased size of the stomatal opening, without any associated decline in water use efficiency.

The AtBBX21-overexpressing plants generated according to the present invention do not reduce water use efficiency. Therefore, no costs associated with a higher transpiration rate exist.

Furthermore, as shown by the present inventors AtBBX21-expressing potato plants had reduced photoinhibition associated with higher production of anthocyanins and phenolic compounds, and higher expression of genes in the phenylpropanoid biosynthesis pathway.

To gain insights into the mechanism of BBX21, the molecular, morphological, metabolic, and photosynthetic behavior in adult BBX21-overexpressing *Arabidopsis* was evaluated. The experiments allowed concluding that BBX21 overexpression improved morphological and physiological attributes, and photosynthetic rates in non-optimal, high-irradiance conditions, without associated impairment of water use efficiency. In addition, it was observed that BBX21-overexpressing potato plants have a better behavior under water stress with higher levels of chlorophylls and higher tuber yield per plant. Under water stress, transgenic plants have higher water use efficiency than wild type control plants.

Therefore, BBX21 was found to be useful for increasing production of potatoes, and seed yield in the Brassicaceae model *Arabidopsis thaliana*.

Consequently, it is an object of the present invention to provide a polynucleotide construct having the sequence of SEQ ID NO: 1; wherein the polynucleotide construct comprises the BBX21 gene from *Arabidopsis thaliana* (AtBBX21 gene) More particularly, the polynucleotide construct allows for the overexpression of the gene AtBBX21 in a crop plant of interest.

Another object of the present invention is to provide a transgenic plant transformed with a polynucleotide construct having the sequence of SEQ ID NO: 1; wherein the transgenic plant is the product of progeny of *Agrobacterium*-mediated transformation using the expression vector pK2GW7 available from Invitrogen, to which the polynucleotide construct of the invention is inserted.

According to a preferred embodiment of the above object of the present invention, the transgenic plant is, without limitation, selected from the group consisting of soybean, sorghum, potato, corn, tomato and barrel clover. More preferably, the crop plant is potato.

According to yet another object of the invention, a method is provided for improving the yield of agronomical crop plants with respect to a control, wild type plant, the method comprising the steps of: (i) providing an agronomical crop plant of interest, (ii) transforming a cell of said agronomical crop plant with a polynucleotide construct having the sequence of SEQ ID NO: 1 according to the present invention, and (iii) growing the transformed agronomical crop plant cell.

Yet another object of the present invention is to provide a method for obtaining a transgenic, stress-tolerant crop plant, comprising the following steps: (i) providing an agronomical crop plant of interest, (ii) transforming a cell of said agronomical crop plant with a polynucleotide construct having a sequence as depicted in SEQ ID NO: 1, and (iii) growing the transformed agronomical crop plant cell; thus obtaining a transgenic, stress-tolerant crop plant, wherein the stress-tolerant crop plant is tolerant to a stress selected from water stress and high-irradiance stress, or a combination thereof.

According to preferred embodiments of the invention, the above method may be applied to a crop plant selected from the group consisting of soybean, sorghum, potato, corn, tomato and barrel clover.

Another object of the present invention is directed to the use of the transgenic event X21 of the invention (BBX21 overexpression in plants) to increase vegetative mass and yield in different crops cultivated under non optimal water conditions (i.e., stress conditions).

The present invention also provides a vector comprising the polynucleotide construct (X21 transgenic event) of the invention, for transforming an agronomical crop plant of interest, thus obtaining a transformed plant overexpressing the BBX21 gene from *Arabidopsis thaliana*.

In a preferred embodiment, the transformation vector is a bacterial vector. More preferably, the bacterial vector is *Agrobacterium tumefaciens* strain GV3101.

According to another object of the present invention, a method is provided for improving plant characteristics, such as increasing green and seed yield, reducing photoinhibition, improving water use efficiency, increasing tuber and chlorophyll production and improving photosynthetic rates, among others, the method comprising transforming a non-transformed plant with the transformation vector of the invention.

In the present invention, the expression "X21 event" is used interchangeably with "BBX21 event" and "AtBBX21 event", where At stands for *Arabidopsis thaliana*. Similarly, transformed plants carrying said event are referred to herein as "BBX21-overexpressing plants" or "X21-overexpressing plants" or "BBX21-OE plants".

BRIEF DESCRIPTION OF THE DRAWINGS

The following figures form part of the present disclosure and are included to further illustrate certain aspects of the present invention.

FIGS. 2A-B. Adult *Arabidopsis* plants of approximately 7-week old (upper panels) and 3-week old (lower panels). (A) Phenotypes of BBX21-overexpressing plants obtained from cDNA (Job N, Yadukrishnan P, Bursch K, Datta S, Johansson H (2018). Two B-Box Proteins Regulate Photomorphogenesis by Oppositely Modulating HY5 through their Diverse C-Terminal Domains. Plant Physiol. 176: 2963-2976). (B) Phenotypes of BBX21-overexpressing plants obtained according to the present invention, by using the complete gene (exons plus introns) as a template for the nucleic acid construct of the BBX21 event.

FIGS. 6A-B: (A) Fresh and (B) dry weight of 35-d-old non-transformed (Spunta) and BBX21-overexpressing potato plants (CH1, CH2, CH13) (n=10 biological replicates). Asterisks indicate significant difference between wild-type and BBX21-overexpressing plants (Students t-test, *P<0.05, ns, not significant).

FIG. 7: Area of the totally expanded leaf in 28-d-old non-transformed (Spunta) and BBX21-overexpressing (CH2, CH3) potato plants (n=10 biological replicates, ns, not significant).

FIGS. 8A-F. Heterologous expression of AtBBX21 promotes stem vasculature and leaf thickening in potato plants. Cross section of (A) apex, (B) middle, and (C) basal stems of non-transformed (Spunta) and transgenic plants (CH2). p, Parenchyma; v, vascular bundle. Bar=50 mm. (D) Layer number of parenchymal cells in Spunta and transgenic lines (CH2, CH13) (n=3). (E) Cross section of leaf lamina in Spunta and CH2 plants. pm, palisade mesophyll cell; sm, spongy mesophyll cells. Bar=50 mm. (F) Leaf lamina width (n=3). n=technical replicates for each genotype. Mean values are shown with error bars indicating SE. Asterisks indicate significant difference between non-transformed and transgenic lines (P, 0.01 and *P, 0.001).

FIGS. 10A-I. Heterologous expression of AtBBX21 increases photosynthesis in potato plants. (A) Chlorophyll levels of non-transformed (Spunta) and transgenic (CH1, CH2, and CH13) potato leaves (n=10). (B) Photosynthesis, (C) transpiration rate, (D) stomatal conductance, and (E) internal concentration of $CO_2$ as a function of photosynthetic photon flux density (PPFD) (n=4). (F) WUE (water use efficiency) as a function of PPFD (n=4). (G) StRCA, (H) StLHCB, and (I) StFTSZ1 transcript levels in non-transformed (Spunta) and transgenic (CH2, and CH13) lines (n=4). n=number of biological replicates. Mean values are shown with error bars indicating SE. Data were analyzed by Student's t tests, and asterisks indicate significant difference between non-transformed and transgenic lines (*P, 0.05, P, 0.01, and *P, 0.001; ns, not significant).

FIGS. 11A-D. Heterologous expression of AtBBX21 increases stomatal aperture in potato leaves. (A) Stomatal density and (B) stomatal index estimated as the number of abaxial stomata/adaxial stomata of non-transformed (Spunta) and transgenic (CH2) potato leaves (n=3). (C) Stomatal aperture of non-transformed (Spunta) and transgenic (CH2) lines (n=3). (D), Representative photographs of stomata in non-transformed (Spunta, left panel) and BBX21-overexpressing (CH2, right panel) lines. S, Stomata; O, opercule. Bar=10 mm. n=number of biological replicates. Mean values are shown with error bars indicating SE. Data were analyzed by Student's t tests, and asterisks indicate significant difference between non-transformed and transgenic lines (*P, 0.05 and ***P, 0.001; ns, not significant).

FIGS. 14A-J. BBX21 overexpression promotes rosette expansion, branching, and accumulation of anthocyanins and phenolics in *Arabidopsis*. (A) Representative photographs showing vegetative rosette (35-d-old plants, left) and (B) secondary flowering ramifications (98-d-old plants, right) in wild-type (Col) and BBX21-overexpressing (BBX21-OE) *Arabidopsis* plants. (C) Leaf length, (D) width of the fourth expanded leaf, and (E) number of secondary flowering axes (n=8). (F) Anthocyanin and (G) phenolic content in leaves (n=5). (H) CHS, (I) CHI, and (J) F3H transcript levels (n=3). n=number of biological replicates. Mean values are shown with error bars indicating SE. Data were analyzed by Student's t tests, and asterisks indicate significant difference between Col and BBX21-OE *Arabidopsis* plants (*P, 0.05, P, 0.01, and *P, 0.001).

FIG. 15A-H. Heterologous expression of AtBBX21 in potato promotes gene expression and metabolites accumulation related with the phenylpropanoid pathway in leaves. (A), Diagram of phenylpropanoid pathway and key enzymes. Transcript levels of (B) PAL, (C) CHS, (D) CHI, and (E) F3H (n=4). (F) Chlorogenic acid 1, (G) chlorogenic acid 2, and (H) quercetin glycoside metabolites measured by HPLC (n=5). n=number of biological replicates. Mean values are shown with error bars indicating SE. Data were analyzed by Student's t tests, and asterisks indicate significant difference between non-transformed and transgenic lines (*P, 0.05; ns, not significant).

FIGS. 16A-H: BBX21 overexpression promotes photosynthesis in *Arabidopsis*. A, Photosynthesis, (B) transpiration rate, (C) stomatal conductance, and (D) internal concentration of $CO_2$ as a function of PPFD (n=4). (E) WUE as a function of PPFD (n=4). Transcript levels of (F) FD1, (G) RCA, and (H) LHCA transcripts (n=3). n=number of biological replicates. Mean values are shown with error bars indicating SE. Data were analyzed by Student's t tests, and asterisks indicate significant difference between Col and BBX21-OE plants (*P, 0.05 and **P, 0.01; ns, not significant).

FIGS. 17A-H: Photographs of 21-d-old non-transformed (left) and BBX21-overexpressing (right) plants Phenotype of non-transformed (wild type, Spunta) and BBX21-overexpressing (CH13) potato plants under (A) white light and (B) simulated shade. (C) Total plant height, (D) internode distance, (F) stem diameter (G) leaf length, (E) anthocyanins and (H) phenolics in plants cultivated in white light (WL) and simulated shade (SS). Mean values are shown with error bars indicating SEM. Asterisks indicate significant difference between non-transformed and BBX21-overexpressing lines (Student's t-test, ns: not significant, *P<0.05, P<0.01, and *P<0.001).

DETAILED DESCRIPTION OF THE INVENTION

Figure 1A:
FIGS. 1A-B. (A) 3-week old and (B) 6-week old adult wild-type (left side of image) and 35s:BBX32-overexpressing (right side of image) *Arabidopsis* plants (prior art).
Figure 1B:

The knowledge around BBX proteins is quite limited by the complexity and modularity of the molecular signaling pathways they are involved in, and the scarce amount of available functional information (Gangappa S N, Botto J F (2014) op. cit.).

As it was disclosed hereinabove, the BBX21 transcription factor belongs to structural group IV and contains two B-box domains. The biological roles for BBX21 had not been explored previously, with the exception of its roles in seed germination and seedling photo-morphogenesis in the *Arabidopsis* model system. In *Arabidopsis*, BBX21 is a potent transcription factor that promotes photo-morphogenesis (Datta S, Hettiarachchi C, Johansson H, Holm M (2007) *SALT TOLERANCE HOMOLOG2, a B-box protein in Arabidopsis that activates transcription and positively regulates light-mediated development*. Plant Cell 19: 3242-3255) and inhibits shade avoidance elongation responses (Crocco et al., (2010) op. cit.).

BBX21 is a pivotal component in the COP1-HY5 regulatory hub that regulates the seedling developmental program during the transition between dark and light (Xu et al., (2018) op. cit.). BBX21 is targeted for 26S proteasome-mediated degradation in darkness, and it is stabilized when seedlings grow in the light, promoting photo-morphogenesis through HY5 activity. Interestingly, BBX21 has also been involved in the promotion of *Arabidopsis* seed germination by interfering with HY5 binding to the ABI5 promoter (Xu et al., (2014) op. cit.).

Despite many works having studied the function of CONSTANS/BBX1, few studies have focused on the functions of other BBX members in crop species (Gangappa and Botto, (2014) op. cit.). The work carried out by the present inventors reveals a role for BBX21 in crop species and its involvement in the regulation of photosynthetic rate and photoprotection responses in potato and *Arabidopsis* adult plants. Previous work showed that heterologous expression of *Arabidopsis* BBX32 in soybean (*Glycine max*) plants increased grain yield by altering the timing of reproductive development and thus extending the period between pod and seed development (Preuss et al., (2012) op. cit.). More recently, it has been demonstrated that BBX24 overexpression in *Chrysanthemum morifolium* produced plants with early flowering and increased tolerance to freezing and drought (Yang Y, Ma C, Xu Y, Wei Q, Imtiaz M, Lan H, Gao S, Cheng L, Wang M, Fei Z, Hong B, Gao J (2014) *A zinc* finger protein regulates flowering time and abiotic stress tolerance in Chrysanthemum by modulating gibberellin biosynthesis. Plant Cell 26: 2038-2054). Considering the results of the work carried out by the present inventors, it is concluded that the overexpression of some members of BBXs (BBX21, BBX24, and BBX32) can contribute to improve crop plant phenotypes, apparently by affecting different physiological features (i.e. phenology, tolerance to stresses, and photosynthesis rates). In the post-green revolution era, optimizing plant energy capture and use is a key target for improvement to increase crop yields. The present invention reveals the importance of BBX21 as a target transcription factor to increase photosynthetic efficiency and reduce photoinhibition by altering anatomical and biochemical features on potato plants with significant positive effects on tuber yield. The use of biotechnological tools to modify the expression levels of the BBX21 transcription factor is proposed herein as a more useful strategy than photoreceptor transgenesis, to avoid non-desirable pleiotropic effects such as the decreased WUE (water use efficiency) previously documented in PHYB-overexpressing lines (Boccalandro H E, Rugnone M L, Moreno J E, Ploschuk E L, Serna L, Yanovsky M J, Casal J J (2009) *Phytochrome B enhances photosynthesis at the expense of water-use efficiency in Arabidopsis.* Plant Physiol 150: 1083-1092) Taking into account the results that were obtained in potato plants cultivated under natural radiation in a greenhouse, the present inventors postulate that enhanced BBX21 levels could be used in breeding programs to increase tuber yield of other commercial potato genotypes.

Finally, it should be mentioned that, besides the different and advantageous agronomic features provided by the BBX21 event, as demonstrated in the present invention, this event also differs from other agronomical events of the state of the art in the methodology used for the generation of the transgenic material. The present inventors have used the complete DNA (genomic DNA or gDNA) of the BBX21 gene, while, the most common procedure in the art is to use the cDNA (complementary DNA) for generating new constructs. In the case of overexpressing the BBX21 gene from cDNA a totally opposite phenotype is observed as compared to the one obtained when working with the complete DNA from BBX21 gene in *Arabidopsis thaliana* (FIG. 2, (A) Job et al (2018) op. cit. and (B) Crocco et al (2018) op. cit.). Comparatively, overexpression of BBX21 from cDNA renders smaller plants when compared to wild type plants, with a lower number of branches and flowers, while overexpression of BBX21 from DNA renders robust plants having a larger size (FIG. 2). Normally, genes selected for heterologous expression are cloned by using the cDNA as a template, which is only comprised of coding DNA. However, when cloning a gene by using DNA as a template, amplification is effected on both exons (coding region) and introns (non-coding region). Many introns may pose relevant functions for mRNA transcription, maturation or edition, and even house non-coding RNA (ncRNA) involved in the regulation of gene expression and cell processes. In humans, several evidences demonstrated that phenotypic variants associated with diseases are the consequence of multiple steps of RNA processing and mRNA dynamics, including splicing, 3'end processing, mRNA structure and stability, translation efficiency and regulation by RNA-binding proteins and by microRNAs (Manning K, Cooper T A (2017) *The roles of RNA processing in translating genotype to phenotype.* Nat Rev Mol Cell Biol. 18: 102-114). According with that, it is hypothesized that the genes cloned from DNA may have different functions than those cloned from cDNA in plants.

EXAMPLES

The invention is further illustrated by the following Examples, which are not intended to limit the scope thereof. Instead, the examples set forth below should be understood only as exemplary embodiments for better taking into practice the present invention.

In the following, all experimental assays were conducted under controlled greenhouse conditions with natural photoperiod and radiation. The greenhouse was located at the Faculty of Agronomy, University of Buenos Aires (34° 35'S, 58° 29'W), with natural radiation (PAR=500 µmol m$^{-2}$ s$^{-1}$) and temperatures ranging between 18° C. and 22° C. The experiments were carried out between March and November with a photoperiod of around 13.5 h.

For the statistical analysis of experimental data, a completely randomized ANOVA design was used. Mean comparisons between control and transgenic lines were done with Student's t test. Analyses were carried out using Prism (GraphPad Software).

Example 1

Obtaining Genomic DNA from Plants and Cloning Protocol for the X21 Event

Young (21-day old) leaf tissue samples from *Arabidopsis thaliana* plants of the Columbia ecotype (Col) were used for this cloning technique. DNA extraction was carried out as follows:

1. Freshly cut green material is ground with liquid N$_2$.
2. Pulverized plant material is placed in a 1.5 ml Eppendorf tube and resuspended with 750 µl CTAB buffer (2×), (2% CTAB, 100 mM Tris base pH 8.0, 10 mM EDTA and 0.7M NAC1, and adding water up to 500 ml and autoclave). Then, 30 µl of 2-13 mercaptoethanol are added. The mixture is stirred gently and incubated for 30 minutes at 65° C.
3. 300 µl potassium acetate (3M, pH 4.8) are added, slightly mixed and incubated on ice for 15 min. The mixture is centrifuged for 10 min at 14,000 rpm and then the supernatant is transferred to a new, clean Eppendorf tube.
4. 500 µl of a mixture of chloroform: isoamylic alcohol (24:1) are added, gently mixed by inverting the tube and centrifuged for 10 min at 14,000 rpm.
5. The upper layer is carefully pipetted to a tube with 500 µl cold isopropanol for precipitating DNA, and then incubated on ice for 60 min.
6. DNA is centrifuged for 5 min at 14,000 rpm and supernatant was discarded.
7. The DNA pellet is washed twice with 500 µl cold 70% ethanol. The remaining ethanol is discarded and the tube is left in a stove at 37° C. for 15 minutes for allowing the DNA to dry completely.
8. DNA is resuspended in 30-50 µl milliQ H$_2$O. DNA amplification by PCR: for amplification of DNA fragments using taq DNA polymerase (Invitrogen).

The cloning of the X21 event was performed via PCR amplification of the At1g75540 locus, using primers (forward and reverse primers as detailed below) containing attB recombination sites.

The forward primer (GatFor172) hybridizes from the ATG transcription initiation codon. The sequence of GatFor172 is depicted below and in the Sequence listing of this application.

Forward primer (GatFor172):

(SEQ ID NO: 2)
5'-GGGGACAAGTTTGTACAAAAAAGCAGGCTCCATGAAGATCAGGTGCGA
CGT-3'

The reverse primer (GatRev_172) includes the STOP codon for the locus within its sequence. The sequence of GatRev_172 is depicted below and in the Sequence listing of this application.

Reverse primer (GatRev_172):

(SEQ ID NO: 3)
5'-GGGGACCACTTTGTACAAGAAAGCTGGGTCTTACCAGAAAGATCTAAA
CT-3'

The conditions for the PCR amplification were as follows: initial cycle at 95° C. for 4 min, followed by 95° C. for 30 secs (denaturing), 54° C. for 1 min (alignment), 72° C. for 1:30 min (extension). 30 cycles were run. The amplified product was separated electrophoretically in a 1% agarose gel with 0.5×TBE. Later, the band corresponding to the molecular weight of event X21 was separated and purified.

The amplification product comprises a sequence string from the ATG initiation codon to the TGA stop codon (termination codon) of the AtBBX21 gene. Thus, said sequence comprises all the open reading frame (ORF) of the AtBBX21 gene, which includes UTRs, exons and introns.

Thus, the cloned sequence for the At1g75540 gene is depicted in the Sequence listing of this application as SEQ ID NO: 4.

Figure 3:
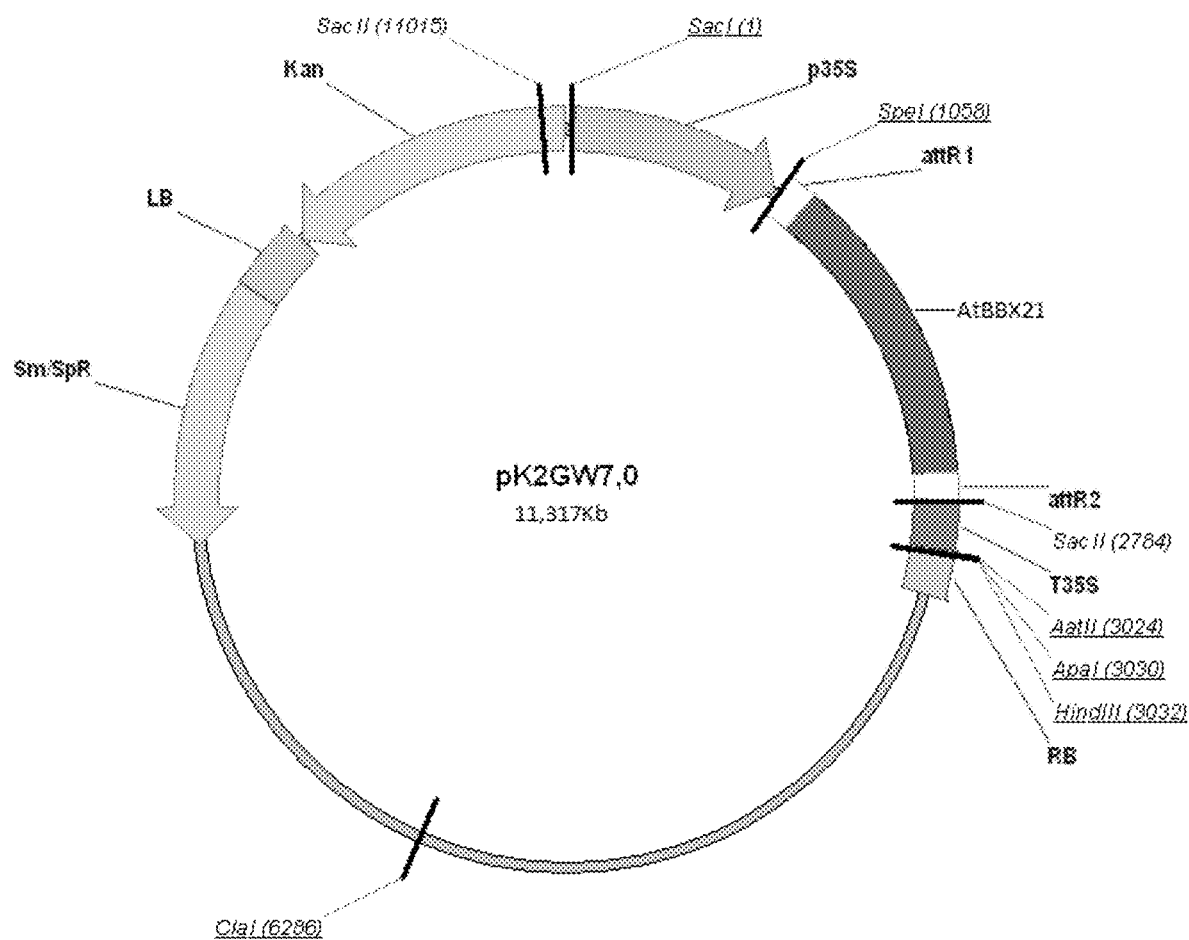
FIG. 3: pk2GW7 plasmid map, showing the different elements of the vector and main restriction sites. LB: left border; Kan: Kanamycin resistance cassette; p35S: 35S promoter; AttR1: recombination site 1; AtBBX21: cloned sequence of BBX21 gene from *Arabidopsis thaliana*; AttR2: recombination site 2; t35S: 35S terminator; RB: right border. The cloned sequence for AtBBX21 (SEQ ID NO: 4) includes initiation codon (ATG), stop codon (TGA), exons and introns. The stretch of sequence from LB to RB is depicted as SEQ ID NO: 1. The complete plasmid is 11317pb in length, its sequence contains the inserted construct of the invention (of SEQ ID NO: 1). The complete sequence of this plasmid is depicted as SEQ ID NO: 35.

The generated PCR fragment (full-length DNA) amplified all the coding region of the BBX21 gene, which was introduced into the pDonor (pDon221) plasmid (Invitrogen) and subsequently, was inserted into an expression vector (pk2GW7) containing the 35s constitutive promoter, using the Gateway cloning technique (Invitrogen). The pk2GW7 vector containing the X21 event was used to transform chemically competent bacteria E. coli Dh5α for amplification. This plasmid vector (pk2GW7) thus contains the polynucleotide construct of SEQ ID NO: 1 for transformation of crop plants of the invention. FIG. 3 shows a map of vector pk2GW7, depicting the different relevant elements of the plasmid.

Selection of the colonies was effected by using a medium containing the antibiotic kanamycin, thus, only those colonies containing the plasmid with the At1g75540 gene correctly inserted survived. This way, several colonies were selected and the presence of the gene was analyzed by colony-PCR using the primers GatFor172 (SEQ ID NO: 2) and GatRev_172 (SEQ ID NO: 3) as disclosed herein above.

Sequencing of three colonies was requested to a specialized facility and the sequences thereof were compared to the one published in the *Arabidopsis* Biological Resource Center database.

One selected colony was cultured in fresh LB media with kanamycin antibiotic, for generating plasmid biomass. Plasmid DNA was purified by miniprep. The resulting purified plasmid DNA was introduced into the *Agrobacterium tumefaciens* strain GV3101 through electroporation. Those bacteria that had incorporated the plasmid with the At1g75540 locus, were selected in solid LB media with the antibiotics kanamycin, spectinomycin and rifampicin. One of these positive colonies during selection was transferred to liquid LB media with the antibiotics kanamycin, spectinomycin and rifampicin. This vector (comprising the polynucleotide construct of SEQ ID NO: 1) was used for transforming *A. thaliana* (see FIG. 4), *Solanum tuberosum* and other plants by the floral dip method as previously described by Bechtold and Pelletier (Bechtold, N. and Pelletier, G. (1998) *In planta Agrobacterium-mediated transformation of adult Arabidopsis thaliana plants by vacuum infiltration*. Methods Mol. Biol. 82, 259-266.).

Figure 4:
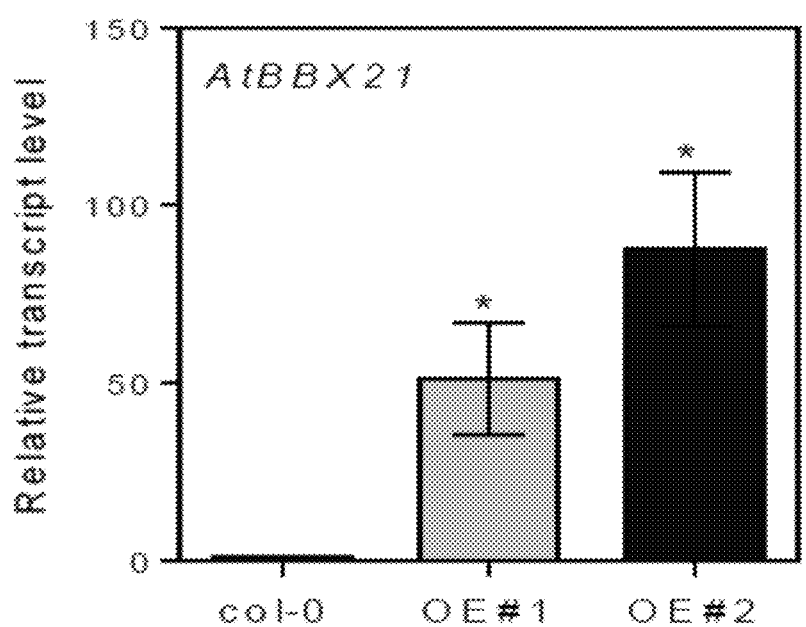
FIG. 4. BBX21 transcript levels in two overexpressing lines of *Arabidopsis* (OE #1 and OE #2). Mean values are shown with error bars indicating SEM. Asterisks indicate significant difference between wild-type (col-0) and BBX21-overexpressing lines (Students t-test, *P<0.05).

FIG. 4 shows the BBX21 transcript levels in wild-type (col-0) and transformed (OE #1 and OE #2) *Arabidopsis* plants, confirming the overexpression of the AtBBX21 gene in those transformed plants that incorporated the construct of the invention, as measured in a quantification assay using AtBBX21 sense and antisense primers (SEQ ID NO: 5 and 6, respectively) listed in Table 1 below.

TABLE 1

| Arabidopsis thaliana BBX21 gene | | |
|---|---|---|
| Gene | code | Primers used for gene quantification |
| AtBBX21 | At1g75540 | AtBBX21 sen: CGACATCTGTCAGGATAAA (SEQ ID NO: 5) |
| | | AtBBX21 ant: GTTCGCAGCGTGGATCGAT (SEQ ID NO: 6) |

Preferably, *Agrobacterium tumefaciens* strain GV3101 is the host for the transformation vector of the invention, containing the BBX21 gene from *A. thaliana*. Transformed crop plants of interest are obtained via *A. tumefaciens*-mediated transformation.

As proven herein, when cloning the BBX21 gene from the genomic DNA of *Arabidopsis thaliana* for overexpressing it in the plant species *Arabidopsis* and potato, a surprising phenotype of high agronomical value is obtained. Also, as shown in the present invention, the phenotypes of *Arabidopsis* plants as obtained when conventional techniques are used for cloning the BBX21 gene, are opposed to those obtained when complete DNA is used, according to the present invention (see, e.g., FIG. 2). The present inventors hypothesize that the non-coding regions may play a regulatory role, not yet described, which provide plants with the advantageous features disclosed herein.

The transgenic plants generated according to the present invention, expressing the BBX21 gene from *Arabidopsis thaliana*, were more robust and produced more tubers than the corresponding wild-type plants. In turn, these plants proved to have higher photosynthetic rates, showed significant increase in photosynthesis gene expression as well as a reduced photoinhibition, without evidencing an associated negative effect in terms of water use efficiency. Similar features are observed when expression of this event is carried out in the model plant *Arabidopsis thaliana* and other crops of agronomic interest, as demonstrated in the examples disclosed herein below.

The BBX21 gene is highly conserved throughout green plants, and physiological evidence has been comparable for *Arabidopsis* and *Solanum*, these being two evolutionary distant species. The BBX21 event may thus be used in other dicotyledonous plants of agronomical interest, for enhancing the yields thereof.

Example 2

Heterologous Expression of AtBBX21 in Potato Plants

Full-length BBX21 was expressed under the control of a 35S promoter in *S. tuberosum* var. *Spunta*. Transgenic potato plants were generated successfully by *Agrobacterium tumefaciens*-mediated transformation. 13 independent transgenic lines were obtained. To confirm the presence of BBX21 in transgenic potato plants, reverse transcription quantitative PCR (RT-qPCR) analysis was conducted for assessing the expression of BBX21 gene. RT-qPCR analysis was performed on an optical 96-well plate using SYBR Green PCR master mix (Applied Biosystems) and an ABI PRISM 7500 real-time PCR system (Applied Biosystems). Gene-specific primer pairs were designed using Beacon Designer 7.0 (Premier Biosoft). The primers used in this work are those mentioned in Example 1. The expression of each gene was normalized to tubulin (TUB) and each treatment was standardized to wild-type expression (see Table 2 below):

TABLE 2

Tubulin gene, standard reference for normalization of expression level

| Gene | Code | Primers used for gene quantification |
|---|---|---|
| TUB | at5g44340 | TUB sen: AACCTCCATTCAGGAGATGTTT (SEQ ID NO: 7) |
|  |  | TUB ant: TCTGCTGTAGCATCCTGGTATT (SEQ ID NO: 8) |

Three independent transgenic lines (CH1, CH2, and CH13) displayed at least 4-fold higher levels of the BBX21 transgene than wild-type Spunta plants (FIG. 5, a and b). These three lines (CH1, CH2, and CH13) were used for further experiments according to the availability of tubers.

Figure 5A:
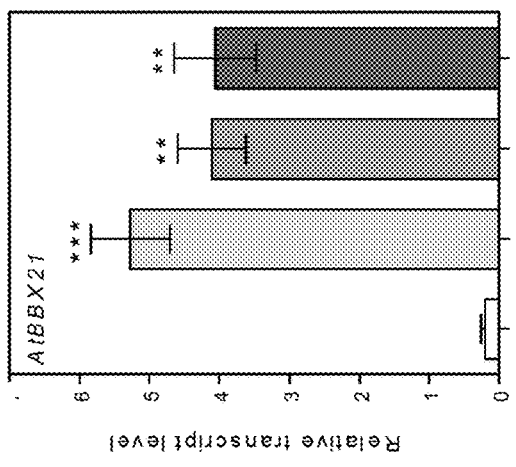
FIGS. 5A-E. Transgenic AtBBX21 potato lines are more robust and shorter than non-transformed plants. (A) Representative photograph of 28-d-old non-transformed (Spunta) and transgenic potato plants (CH1, CH2, and CH13). (B) AtBBX21 transcript levels of the three independent transgenic lines (CH1, CH2, and CH13) used in this study with respect to non-transformed line (Spunta) (n=10). (C) Plant height and (D) stem diameter in 21-d old transgenic potato plants (CH1, CH2, and CH13) and non-transformed plants (Spunta) (n=10). (E) Fresh weight relative to dry weight in 35-d-old transgenic potato plants (CH1, CH2, and CH13) and non-transformed plants (n=10). n=number of biological replicates. Mean values are shown with error bars indicating SE. Asterisks indicate significant difference between non-transformed and transgenic lines (*P, 0.05, P, 0.01, and *P, 0.001).
Figure 5B:
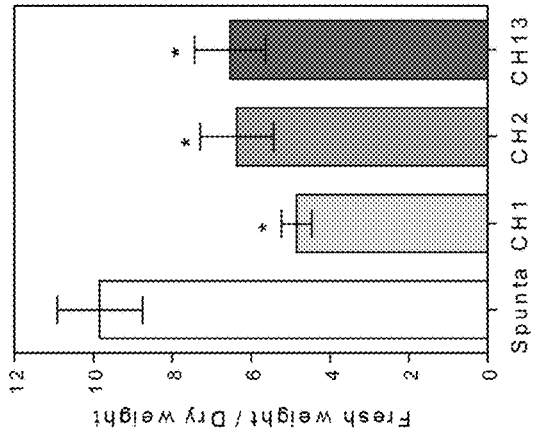
Figure 5C:

Transgenic and non-transformed plants were grown under natural radiation, a photoperiod of 13.5 h light, and a controlled temperature between 18 and 22° C. in a greenhouse for 21 d. BBX21-overexpressing plants were on average significantly shorter and had significantly wider basal stems than control Spunta plants (P, 0.001; FIG. 5c).

Figure 5D:
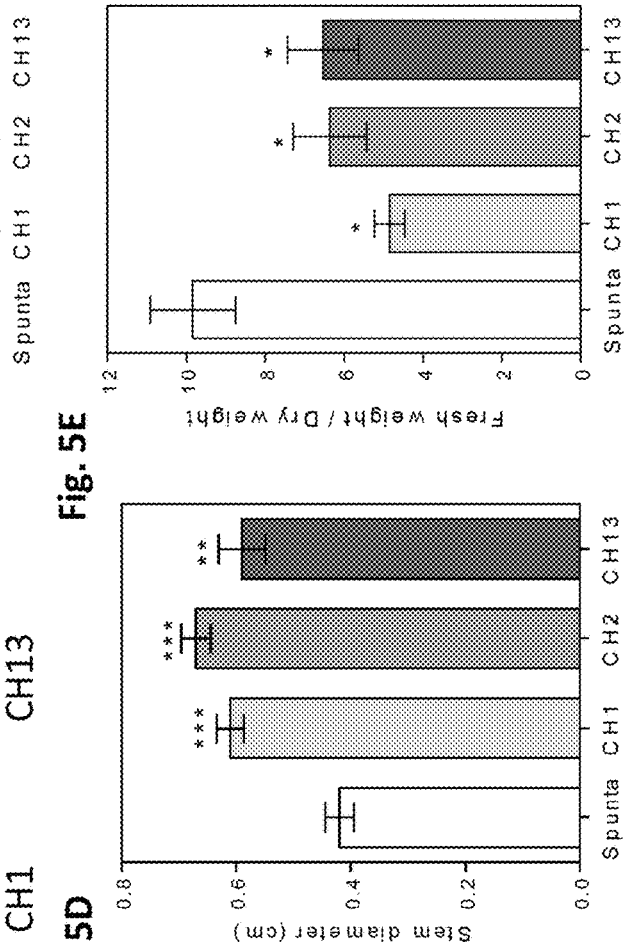
Figure 5E:
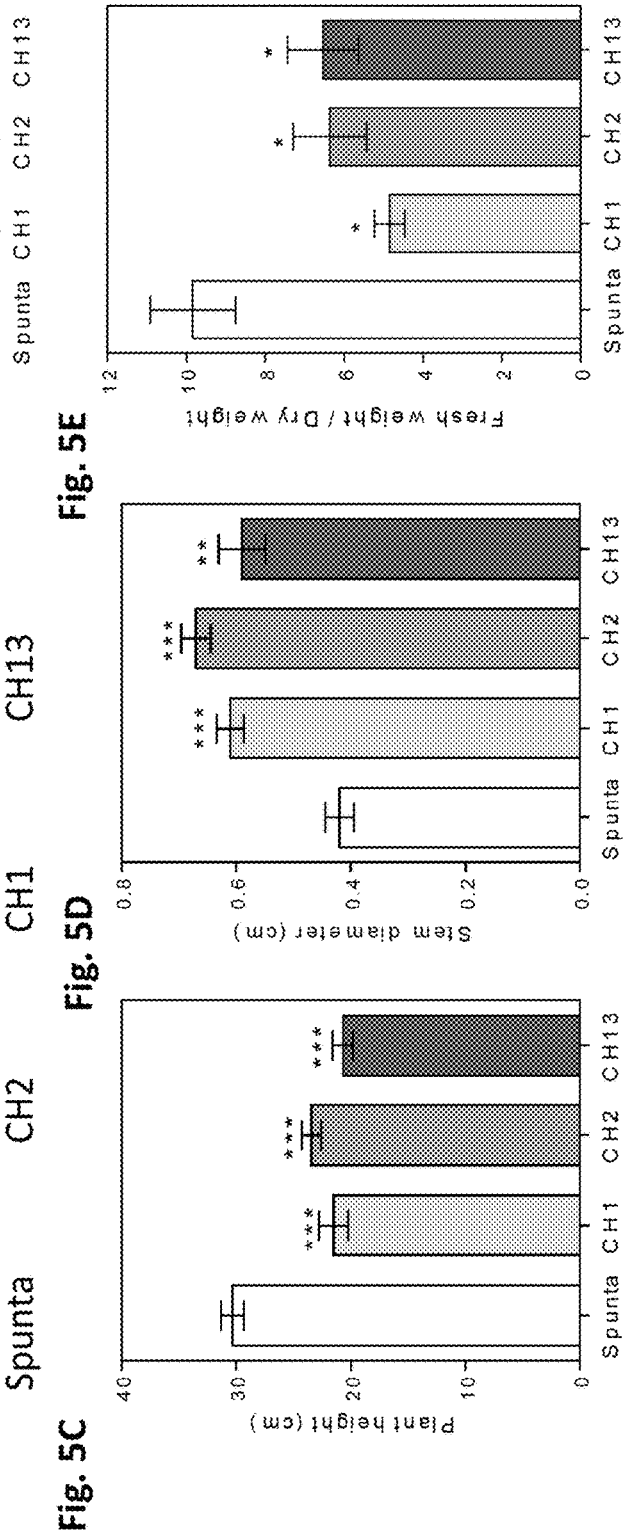

By the end of the experiment, BBX21-overexpressing plants showed a significant reduction in the fresh/dry weight ratio compared with the control and consequently had a higher dry weight (FIG. 5d; FIG. 6). In addition, no differences were detected in the leaf area between genotypes (FIG. 7). Transgenic plants showed a wider vasculature (FIG. 8) and more layers of parenchyma cells than control plants (FIG. 8, a and b). These features were observed in the apical, medium, and basal sections of the stem (FIG. 8a). In addition, transgenic plants had slightly thicker leaf blades than control plants (FIG. 8c).

Figure 9A:
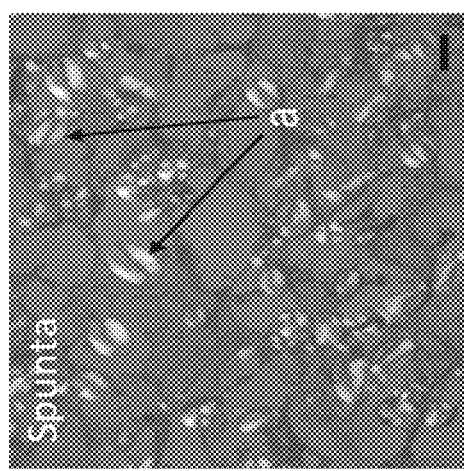
FIGS. 9A-J. Heterologous expression of AtBBX21 increases tuber yield in potato plants. Representative photographs of (A) non-transformed (Spunta) and (B) transgenic (CH2) tubers at the end of the experiment. (C) Tuber weight of non-transformed (Spunta) and transgenic (CH2) plants. (D) Tuber number (n=12) of non-transformed (Spunta) and transgenic (CH2) plants. (E) Starch content (n=5) of non-transformed (Spunta) and transgenic (CH2) plants. (F) Amyloplast length of non-transformed (Spunta) and transgenic (CH2) plants. (G) Amyloplast width of non-transformed (Spunta) and transgenic (CH2) plants. (H) Amyloplast number (n=3) of non-transformed (Spunta) and transgenic (CH2) plants. Cross section of tubers of (I) non-transformed (Spunta) and (J) transgenic (CH2) plants. a, Amyloplast. Bar=10 mm. n=number of biological replicates. Mean values are shown with error bars indicating SE. Data were analyzed by Student's t tests, and asterisks indicate significant difference between non-transformed and transgenic lines (*P, 0.05, P, 0.01, and *P, 0.001; ns, not significant).
Figure 9B:
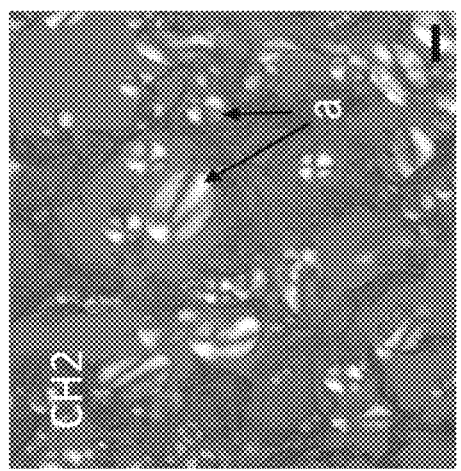
Figure 9C:
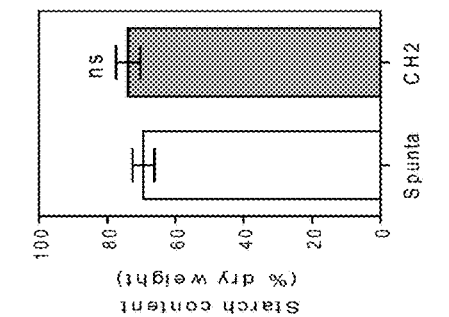

The present inventors hypothesized that the anatomical and morphological differences of BBX21-overexpressing plants could affect tuber yield at harvest. In an independent experiment, the number and weight of tubers was evaluated in transgenic and non-transformed plants at harvest. It was found that transgenic plants had a 15% higher tuber yield and smaller tubers compared to control plants (FIG. 9, a and b). However, the tuber quality in terms of starch content was similar between genotypes (FIG. 9b). In addition, the number of amyloplasts contained in the tubers of transgenic lines was lower than in control Spunta plants, and the length and width of amyloplasts were higher than control plants (FIG. 9, c and d).

Therefore, based on this assay, it is clearly demonstrated that the heterologous expression of *Arabidopsis* BBX21 in potato resulted in short, robust plants with a higher tuber yield than non-transformed plants.

Example 3

Study of Photosynthesis in AtBBX21-Expressing Plants

The present inventors speculated that the higher levels of chlorophyll detected in transgenic plants (FIG. 10a) may reflect improved photosynthesis. So, the net photosynthetic rate and related photosynthetic traits in 28-d-old plants was measured.

For this experiment, measurements were carried out in an open infrared gas analysis system (Li-Cor 6400). Light functions were measured at 0, 30, 50, 100, 200, 300, 400, 500, 750, 1,000, 1,500, and 2,000 mmol m22 s21. Photosynthetic photon flux density (PPFD) was done in fully expanded leaves using the 6400-02B LED light source chamber. Air flow and $CO_2$ concentration in the reference cell ($CO_2R$) were automatically controlled by the equipment at 300 mmol s21 and 400 mmol s21 (ppm), respectively. Water use efficiency was estimated as the ratio of carbon assimilation and transpiration (net photosynthesis rate/transpiration rate).

It was found that transgenic lines had higher photosynthetic rates than control Spunta plants between 400 mmol $m^{-2}$ $s^{-1}$ and 2,000 mmol $m^{-2}$ $s^{-1}$ PPFD, although no differences were found between genotypes under non-saturating PPFD quantum yields (see slopes in FIG. 10b). In addition, these plants showed higher transpiration rates and stomatal conductance (FIG. 10b).

Interestingly, the water use efficiency (WUE) was similar between genotypes, indicating that the higher photosynthetic rates of transgenic lines did not affect WUE (FIG. 10c). In addition, a positive relationship was found between higher rates of photosynthesis and an increase in the expression of the RCA (Rubisco ACTIVASE), but not LHCB (LIGHT-HARVESTING CHLOROPHYLL-B) or FTSZ1 (PLASTID-DIVIDING RING) photosynthetic genes (FIG. 10d).

Figure 9D:
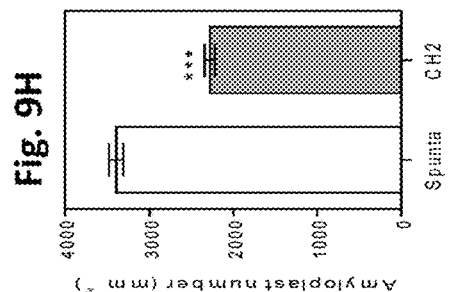
Figure 9E:
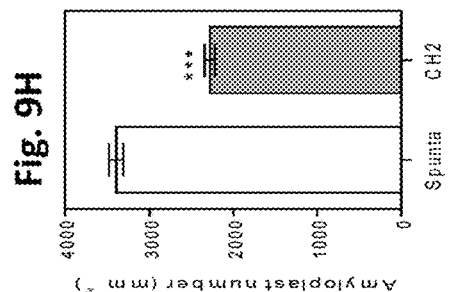
Figure 9F:
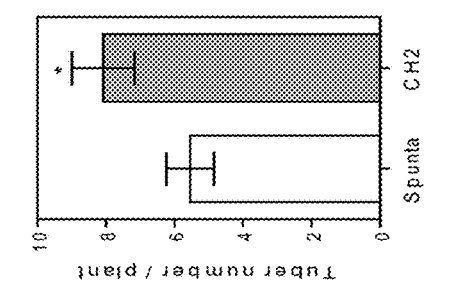
Figure 9G:
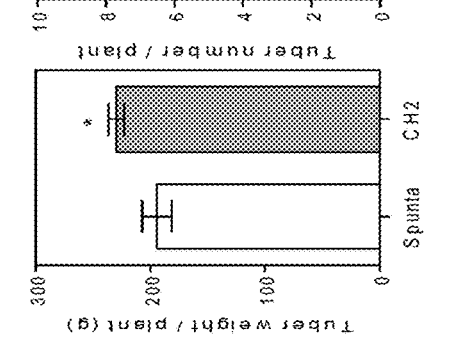
Figure 9H:
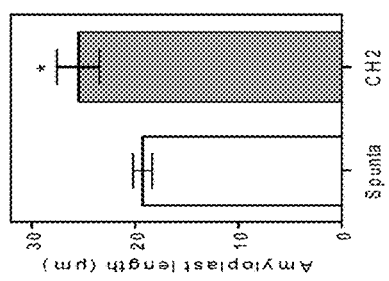
Figure 9I:
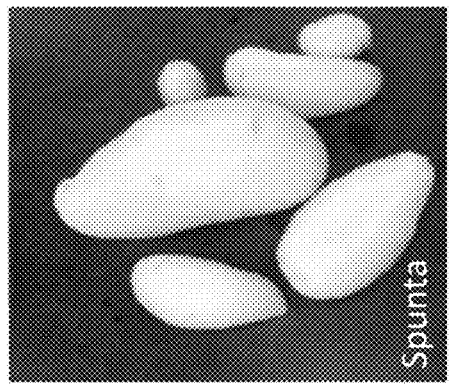
Figure 9J:
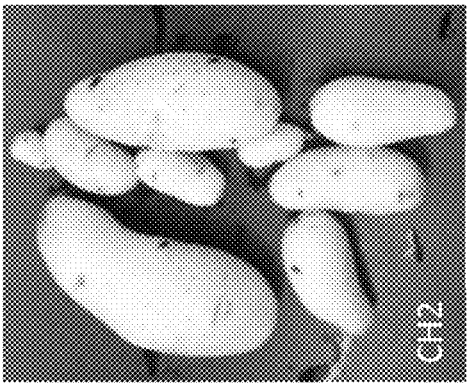

The following table 3 shows the photosynthesis genes measured in FIG. 9d for potato.

TABLE 3

*Solanum Tuberosum*-Photosynthesis genes.

| Gene | Code | Primers used for gene quantification |
|---|---|---|
| StLHCB1 | PGSC0003DMG400008299 | StLHCB1 sen: TCTTGGCCATCTGGGCTTGC (SEQ ID NO: 9) StLHCB1 ant: TGGGTCAAAGCTGCCACCAG (SEQ ID NO: 10) |
| StRCA | PGSC0003DMT400049256 | StRCA1 sen: ACTGGGCACCAACCAGAGAA (SEQ ID NO: 11) StRCA1 ant: AGGGAAGGCATCGACAAGCC (SEQ ID NO: 12) |
| StFTSZ1 | PGSC0003DMG400022200 | StFtsz1 sen: CAGTCTGCTGCCGAGAACCC (SEQ ID NO: 13) StFtsz1 ant: GACTCCTCCGCTGCCTGTTC (SEQ ID NO: 14) |

Figure 12D:
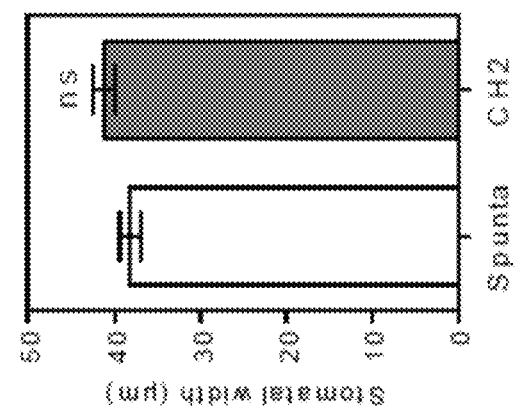
FIGS. 12A-D: Stomatal number in the (A) abaxial and (B) adaxial position of non-transformed (Spunta) and BBX21-overexpressing (CH2) lines. (C) Stomatal length and (D) stomatal width of Spunta and CH2 plants (n=3 biological replicates). Mean values are shown with error bars indicating SEM. Asterisks indicate significant difference between non-transformed and BBX21-overexpressing lines (Student's t-test, *P<0.05 and ***P<0.001, ns, not significant).
Figure 12C:
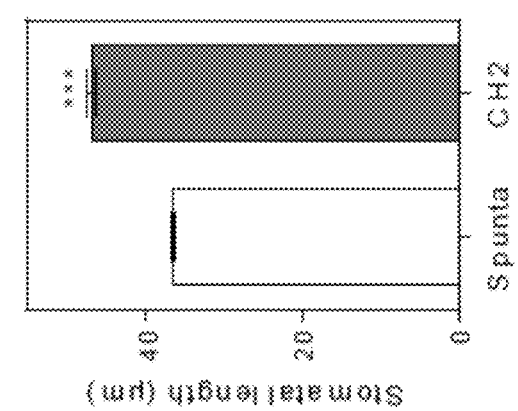
Figure 12B:
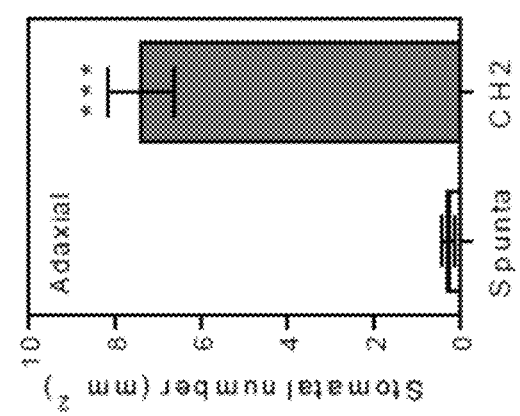
Figure 12A:
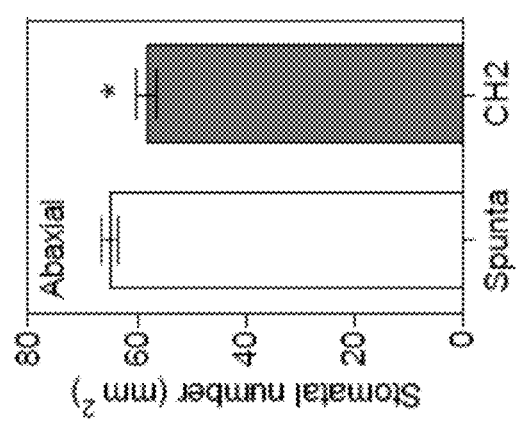

In addition, the increase of photosynthetic activity in transgenic lines compared with non-transformed plants could be associated with stomatal differences. Although the number of stomata was similar between genotypes, significant differences were found in the distribution of stomata in the leaf (FIG. 11a). The level of anphistomy (the increase of stomata density more intensively in the adaxial than in the abaxial side of the leaf) was higher in transgenic lines than control plants. This was indicated by a reduction in the stomatal index, calculated as the density of abaxial stomata/adaxial stomata (FIG. 11a; FIG. 12a). More interestingly, the stomatal area was significantly higher in transgenic plants than in control plants (FIG. 11, b and c). This increase was associated with a higher stomata length but did not show a relationship with stomata width (FIG. 12b). Thus, the higher stomatal area probably contributed to the increased photosynthetic activity observed in transgenic plants (FIG. 10b).

In conclusion, transgenic potato plants had a higher photosynthetic rate and stomatal conductance, which was associated with a larger stomatal opening.

Example 4

Determination of Photoinhibition in Transgenic Plant Leaves

A classical photomorphogenic response is the synthesis of anthocyanins when plants are exposed to light (Mancinelli A L, Rossi F, Moroni A (1991) *Cryptochrome, phytochrome, and anthocyanin production*. Plant Physiol 96: 1079-1085). The abundance of anthocyanins and phenolic compounds was measured in 21-d-old transgenic and non-transformed plants.

Figure 13C:
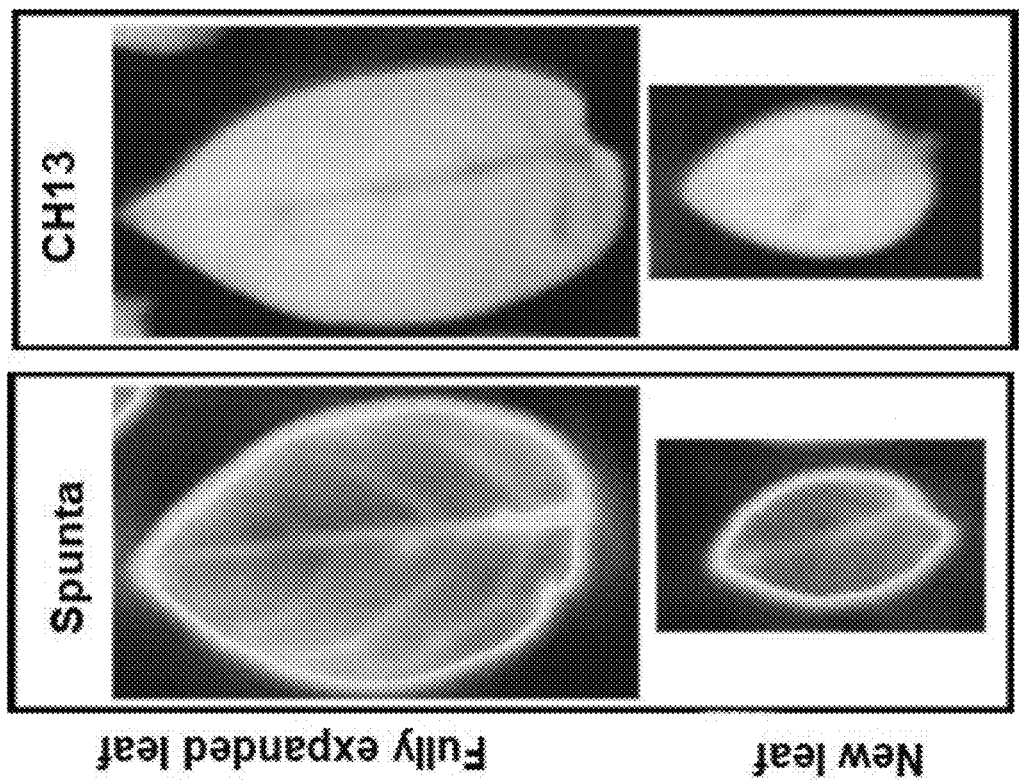
FIGS. 13A-D. Heterologous expression of AtBBX21 increases anthocyanin and phenolic levels in potato leaves. (A) Phenolics and (B) anthocyanins content in non-transformed (Spunta) and transgenic (CH1, CH2, and CH13) potato leaves (n=5). (C), Sunscreen pigment accumulation in young and totally expanded leaves. Sunscreen accumulation is revealed by a decrease in the intensity of UV-induced chlorophyll fluorescence (less fluorescence indicates higher accumulation of anthocyanin and phenolic compounds). (D) Maximal photochemical efficiency (Fv/Fm) in 14-d-old plants acclimated at low irradiance (200 mmol m22 s21) and then exposed at high irradiance (900 mmol m22 s21) for 2 h (n=6). n=number of biological replicates. Mean values are shown with error bars indicating SE. Data were analyzed by Student's t tests, and asterisks indicate significant difference between non-transformed and transgenic lines (*P, 0.05 and **P, 0.01; ns, not significant).
Figure 13B:
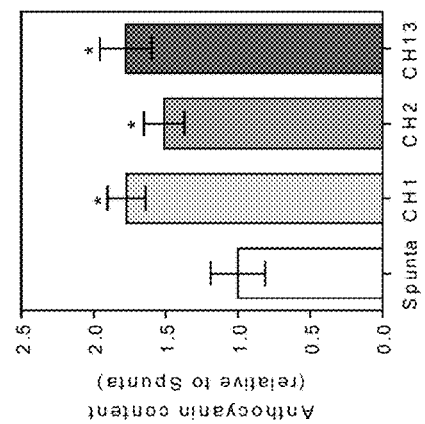
Figure 13A:
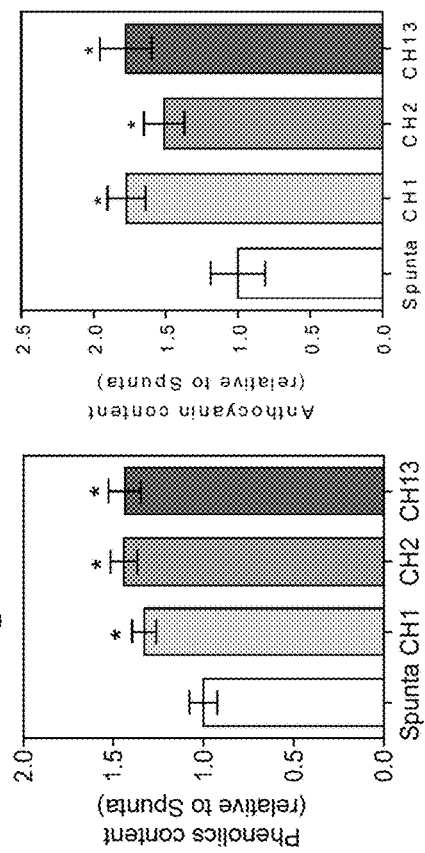
Figure 13D:
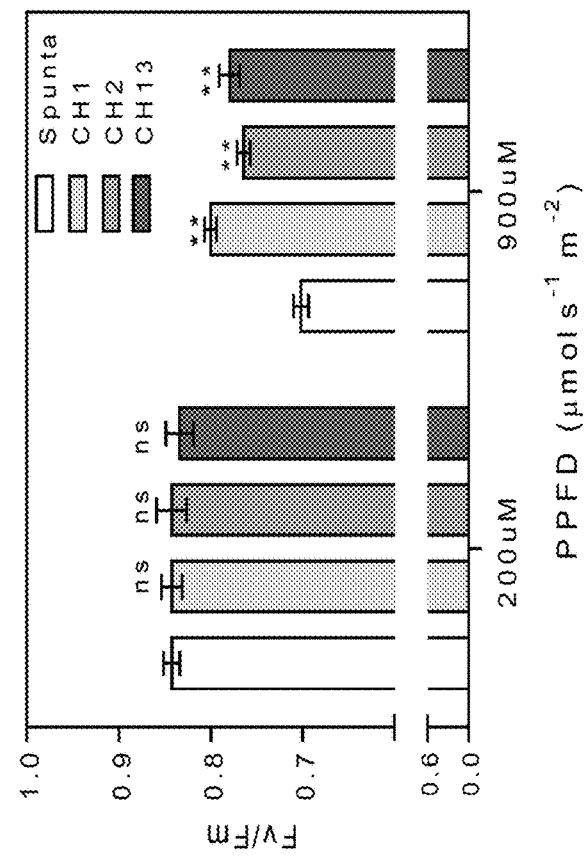

The three transgenic lines showed a significant increase in anthocyanin and total phenolic compound levels (FIG. 13(a)), and this correlated with a lower fluorescence in the leaves (FIG. 13(b)).

Previous studies reported that the increase in anthocyanin and phenols levels in the leaves improve the photoprotection at high irradiance (Gould K S, Kuhn D N, Lee D W, Oberbauer S F (1995) *Why leaves are sometimes red*. Nature 378: 241-242; Manetas Y, Drinia A, Petropoulou Y (2002) *High contents of anthocyanins in young leaves are correlated with low pools of xanthophyll cycle components and low risk of photoinhibition*. Photosynthetica 40: 349-354; Steyn W J, Wand S J E, Holcroft D M, Jacobs G (2002) *Anthocyanins in vegetative tissues: a proposed unified function in photoprotection*. New Phytol 155: 349-361; Harvaux M, Kloppstech K (2001) *The protective functions of carotenoid and flavonoid pigments against excess visible radiation at chilling temperature investigated in Arabidopsis npq and tt mutants*. Planta 213: 953-966). To evaluate this possibility, an experiment with 14-d-old plants that were acclimated at a low irradiance (200 mmol m22 s21) and then exposed to high irradiance (900 mmol m22 s21) for 2 h was carried out. The photoinhibition of photosystem II was estimated by measuring the maximal photochemical efficiency of photosystem II (Fv/Fm) at both levels of irradiance. It was found that Fv/Fm was similar between genotypes at low irradiance, but the photoinhibition of the photosystem II was higher in non-transformed plants than in transgenic plants exposed to high irradiance (FIG. 13(c)).

Although anthocyanin and phenolic contents were higher in BBX21-overexpressing transgenic potato and *Arabidopsis* plants, a similar potential quantum yield was observed when transgenic or non-transformed plants were subjected to low acclimation radiation (i.e. Fv/Fm around 0.85; FIG. 13). Interestingly, a protective effect of these pigments was observed in BBX21-overexpressing plants after exposure to high PPFD, since only non-transformed plants were photoinhibited (Fv/Fm dropped below 0.7; FIG. 13(c)). These results suggest that the reduced photoinhibition of photosystem II in transgenic potato plants may be associated with the accumulation of photoprotective metabolites, leading to a higher photosynthetic rate. It was demonstrated that high transcript levels of several genes involved in the phenylpropanoid pathway (PAL1, CHS, and F3H) led to an increase in anthocyanin and phenolic compound levels in potato and *Arabidopsis* plants (FIGS. 13 and 14).

The table 4 below shows the genes involved in the phenylpropanoid biosynthesis that were measured in wild-type and transformed *Arabidopsis thaliana* plants, as shown in FIG. 14D:

TABLE 4

*Arabidopsis thaliana*-phenylpropanoid biosynthesis genes

| Gene | Code | Primers used for gene quantification |
|---|---|---|
| AtF3H | AT3G51240 | AtF3H sen: AAGGTTGGGTGAAAGTGACG (SEQ ID NO: 15) <br> AtF3H ant: TCAGTGTGACGCTTGAGTCC (SEQ ID NO: 16) |
| AtCHI | AT3G55120 | AtCHI sen: CGGGATCGCTGTGATCGAGA (SEQ ID NO: 17) <br> AtCHI ant: GCCAGGTGACACACCGTTCT (SEQ ID NO: 18) |
| AtCHS | AT5G13930 | AtCHS sen: CGGCGTCGACATGCCTGGTG (SEQ ID NO: 19) <br> AtCHS ant: AGTACCGCCGGCGAAGCAAC (SEQ ID NO: 20) |

Interestingly, the induction of a photoprotective acclimation mechanism to avoid the photosystem damage against excess visible radiation that is mediated by UV/blue light-absorbing flavonoids has been previously demonstrated using non-photochemical quenching mutants of *Arabidopsis* (Harvaux and Kloppstech (2001) op. cit.). In accordance with the present results, PHYB overexpression increased the resistance of the potato photosynthetic apparatus to UV-B, which was associated with a higher accumulation of chlorophylls, carotenoids, and flavonoids in the leaves (Kreslavski V D, Kosobryukhov A A, Shmarev A N, Aksenova N P, Konstantinova T N, Golyanovskaya S A, Romanov G A (2015) *Introduction of the Arabidopsis PHYB gene increases resistance of photosynthetic apparatus in transgenic Solanum tuberosum plants to UV-8 radiation*. Russ J Plant Physiol 62: 204-209).

On average, the Fv/Fm was reduced by around 25% in control plants and 10% in the three transgenic lines. These results suggest a role for BBX21 in protecting against high irradiance, probably by inducing the accumulation of anthocyanin and phenolic compounds in their leaves.

In conclusion, plants generated according to the invention exhibited reduced photoinhibition, which was related to a higher production of anthocyanins and phenolics, as well as an increase in expression of phenylpropanoid biosynthesis genes.

Example 5

Phenylpropanoid Signaling Pathway

The phenylpropanoid signaling pathway induces the accumulation of flavonol glycosides, anthocyanin derivates, and chlorogenic acid by activating the expression of specific enzymes (FIG. 15a).

In the present example, the expression of PAL1 (PHE AMMONIA LYASE1), CHS (CHALCONE SYNTHASE), CHI (CHALCONE ISOMERASE), and F3H (FLAVANONE 3-HYDROXYLASE) was evaluated with RT-qPCR, as well as the accumulation of two chlorogenic acids and quercetin glycoside metabolites with HPLC.

The table 5 below shows the genes involved in the phenylpropanoid biosynthesis pathway that were measured in FIG. 15b.

TABLE 5

Solanum Tuberosum-genes of the phenylpropanoid biosynthesis pathway.

| Gene | Code | Primers used for gene quantification |
|---|---|---|
| StCHS | PGSC0003DMT400022261 | StCHS sen: CTATGGCAATATGTCAAGT (SEQ ID NO: 21) StCHS ant: CTTCACCTGTAGTTCCTA (SEQ ID NO: 22) |
| StF3H | PGSC0003DMT400031149 | StF3H sen: ACATTCGGATCCTGGTGGCA (SEQ ID NO: 23) StF3H ant: GTTGTTGCGTCGGACCTGAA (SEQ ID NO: 24) |
| StCHI | PGSC0003DMG400028325 | StCHI A sen: TGCCCTTGACGGGTAAGCAA (SEQ ID NO: 25) StCHI A ant: GGCACCAGGTGGGAAGGTTT (SEQ ID NO: 26) |
| StPAL1 | PGSC0003DMT400080765 | StPAL1 sen: CATCTCCACAATGGCTTGG (SEQ ID NO: 27) StPAL1 ant: TTGGAAGTTGCCACCATGT (SEQ ID NO: 28) |

In general terms, all of these were higher in leaves of transgenic plants than control plants with the exception of CHI expression (FIG. 15, b and c).

These results explain the higher levels of anthocyanins and phenolic compounds in transgenic potato plants compared to non-transformed plants, as was determined in Example 4.

Example 6

Rosette Expansion, Branching, and Accumulation of Anthocyanin and Phenolic Compounds in *Arabidopsis* Plants To gain insight into the role of BBX21 in adult plants, two BBX21-overexpressing *Arabidopsis* lines (BBX21-OE #1 and OE #2) and the wild-type control (Col-0) were cultivated in a greenhouse with natural radiation.

It was found that BBX21-OE lines produced bigger rosettes with longer and wider leaves than Col-0 (FIG. 14, A and B). In addition, BBX21-OE plants showed profuse flowering with a significantly higher number of secondary axes and seed yield than wild-type plants (FIG. 14A; data not shown). The levels of anthocyanins and phenols were evaluated in 35-d-old *Arabidopsis* plants and it was found that BBX21-OE plants produced higher levels of anthocyanins and phenols (FIG. 14C), corroborating the results observed in heterologous expression of AtBBX21 in potato plants. Accordingly, the gene expression of CHS, F3H, and CHI was significantly higher in BBX21-OE than control plants (FIG. 14D).

In other experiments, the photosynthesis rates of BBX21-OE and wild-type plants cultivated in a greenhouse were examined. 35-d-old *Arabidopsis* plants were exposed to different PPFDs and net photosynthesis rates and related photosynthetic traits were evaluated. It was found that BBX21-OE plants showed higher photosynthesis rates, transpiration rates and stomatal conductance than wild-type plants at high irradiances (200 mmol m$^{-2}$ s$^{-1}$; FIG. 16A). In accordance with the inventor's data in potato plants, the WUE was similar between genotypes (compare FIGS. 16B and 10c).

The following table 6 shows the genes involved in photosynthesis for *Arabidopsis thaliana* in FIG. 15C.

TABLE 6

Arabidopsis Thaliana-Photosynthesis genes.

| Gene | Code | Primers used for gene quantification |
|---|---|---|
| AtRCA1 | AT2G39730 | AtRCA sen TCGTTGAGAGCCTTGGAGTT (SEQ ID NO: 29) AtRCA ant CTGAGGTAGGTCTCGGCAAG (SEQ ID NO: 30) |
| AtFD1 | AT1G10960 | AtFD1sen AAGAGGTCGAATGCGAAGAA (SEQ ID NO: 31) AtFD1ant GTCGGATAAGCCACACAGGT (SEQ ID NO: 32) |
| AtLHCA1 | AT3G54890 | AtLHCA1 sen CGCTTATGAGCTGTGGCATA (SEQ ID NO: 33) AtLHCA1 ant CGCTGGAACTTCTTCAAGTC (SEQ ID NO: 34) |

The expression of FD1 (FERRODOXIN-1) and RCA photosynthetic genes showed higher levels in BBX21-OE plants than in wild-type plants, as expected for the higher activity of the photosynthetic apparatus (FIG. 16C).

In conclusion, some of these features (photoinhibition and production of anthocyanins and phenolics) were confirmed in mature BBX21-overexpressing *Arabidopsis* lines.

It was also demonstrated that high transcript levels of several genes involved in the phenylpropanoid pathway (PAL1, CHS, and F3H) led to an increase in anthocyanin and phenolic compound levels in potato and *Arabidopsis* plants.

Photosynthesis/PPFD relationships revealed that both heterologous expression of AtBBX21 in potato plants and BBX21-overexpressing *Arabidopsis* lines dramatically increased photosynthetic rates by up to 60% under saturating irradiances without altering quantum yield (FIGS. 10b and 16A). In addition, RCA and FD1 photosynthesis related genes were up-regulated in both BBX21-overexpressing potato and *Arabidopsis* plants (FIGS. 10d and 16C). These responses were closely related to stomatal conductance and the higher internal CO2 concentration in BBX21-overexpressing transgenic *Arabidopsis* and potato plants, suggesting that stomatal aperture is the major causal effect of the higher photosynthesis rate (Flexas J, Ribas-Carbó M, Bota J, Galmés J, Henkle M, Martínez-Cañellas S, Medrano H (2006) *Decreased Rubisco activity during water stress is not induced by decreased relative water content but related to conditions of low stomatal conductance and chloroplast $CO_2$ concentration.* New Phytol 172: 73-82). Although the stomatal distribution in the leaves differed between transgenic and non-transformed plants, no differences in the number of stomata were observed. Therefore, the effect of stomatal abundance is not associated with the higher photosynthesis rate observed in BBX21-overexpressing plants (FIGS. 10 and 16). These results suggest that radiation use efficiency may be higher in a BBX21-overexpressing potato crop depending on plant architecture and light extinction across the canopy.

BBX21-overexpressing potato and *Arabidopsis* plants had enhanced rates of $CO_2$ uptake and transpiration as well as an increase in stomatal conductance without any associated negative effect on WUE (FIGS. 10c and 16B). An enhanced photosynthetic rate was previously observed in PHYTOCHROME B (PHYB)-overexpressing potato and *Arabidopsis* plants (Thiele A, Herold M, Lenk I, Quail P H, Gatz C (1999) *Heterologous expression of Arabidopsis phytochrome B in transgenic potato influences photosynthetic performance and tuber development.* Plant Physiol 120: 73-82; Boccalandro H E, Ploschuk E L, Yanovsky M J, Sánchez R A, Gatz C, Casal J J (2003) *Increased phytochrome B alleviates density effects on tuber yield of field potato crops.* Plant Physiol 133: 1539-1546; Boccalandro et al., (2009) op. cit.). However, in contrast to BBX21 overexpression, PHYB overexpression reduced the WUE in *Arabidopsis* plants (Boccalandro et al., (2009) op. cit.). Considering that BBX21 overexpression in potato and *Arabidopsis* did not affect the WUE (FIGS. 10c and 16B), the results obtained herein suggest a partial cross talk between BBX21 and PHYB signaling pathways. Several genes have been found to be involved in traits associated with WUE. The expression of some genes can increase or decrease the expression of others, forming a complex network of interactions. Such complex networks involve genotype-by environment interactions as well as epistatic interactions.

Example 7

Study of Stem Elongation of Transgenic Plants Under Simulated Shade

As it was previously demonstrated by the present inventors, BBX21 inhibits shade avoidance responses in *Arabidopsis* seedlings (Crocco et al., (2010) op. cit.). Thus, the authors hypothesize that the heterologous expression of AtBBX21 in potato plants might display a reduced shade avoidance response because of the reduced cell elongation in the stems.

To test this, 21-d-old potato plants were cultivated under either white light or simulated shade in a growth chamber. As expected, a significantly reduced shade avoidance response for internode stem elongation in transgenic plants was observed in comparison to control plants (FIG. 17). In addition, transgenic plants showed a constitutive phenotype with shorter and wider stems than non-transformed plants independently of light treatments.

Interestingly, transgenic plants showed constitutively high levels of anthocyanins and phenols that were independent of light treatment. In opposition, the abundance of these compounds increased in control plants under shade.

Example 8

Determination of Physiological Parameters of Transgenic Plants Grown Under Hydric Restriction Conditions Potato is known to be a water-stress-sensitive crop. The present inventors decided to study the behavior of the transgenic potato lines obtained according to the invention in a hydric restriction assay.

Figure 18:
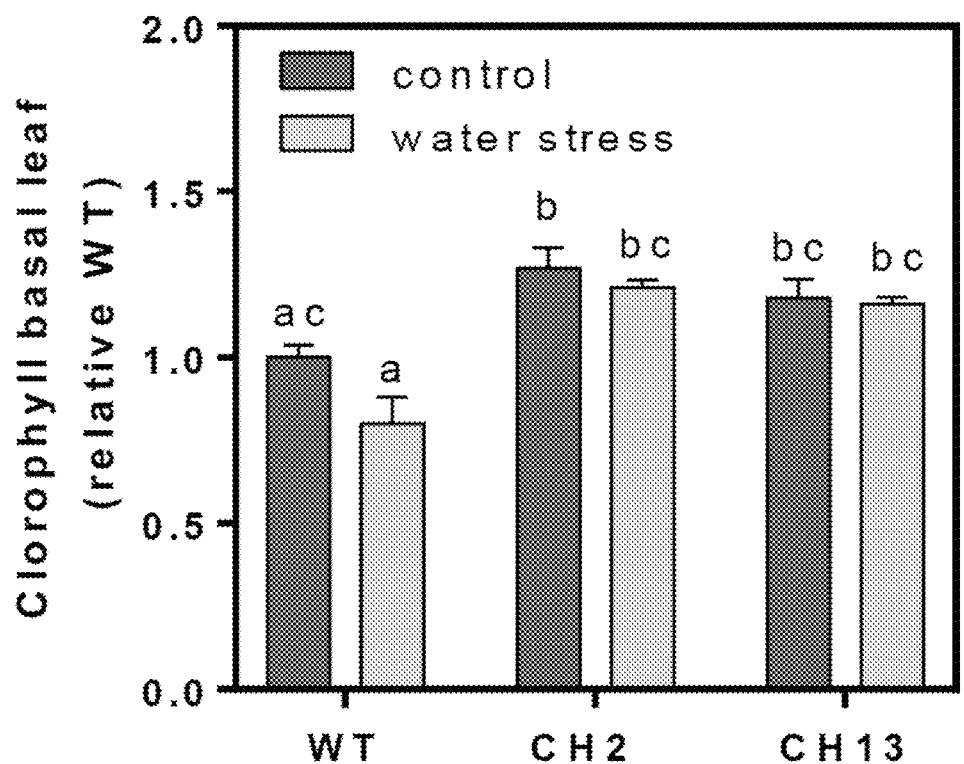
FIG. 18: Heterologous expression of AtBBX21 increases chlorophyll levels in transgenic (CH2, and CH13) potato leaves (n=10) under water stress conditions (65% water restriction with respect to water field capacity, 100% water, control condition).
Figure 19:
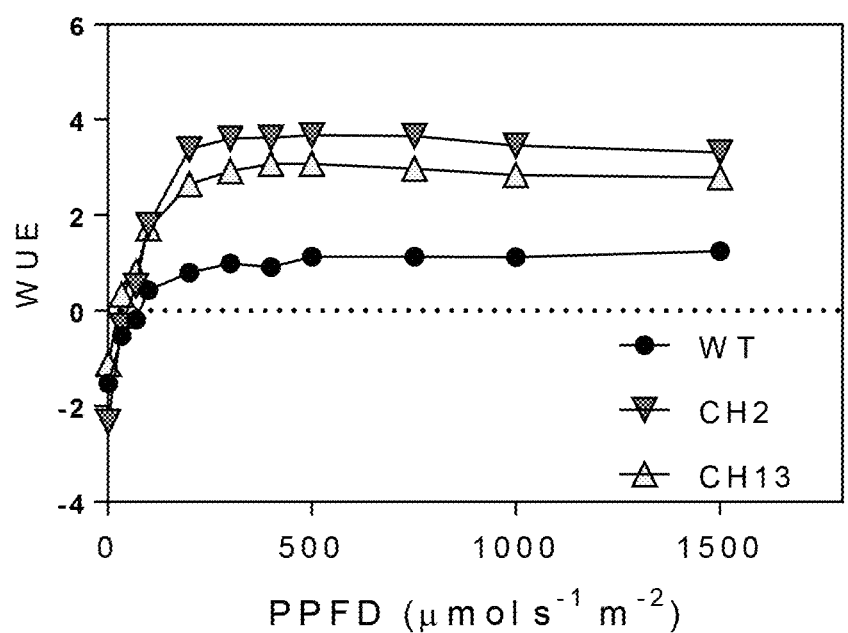
FIG. 19: Heterologous expression of AtBBX21 increases Water Use Efficiency (WUE) in upper leaves of BBX21-overexpressing potatoes (CH2 and CH13) cultivated under water stress conditions of 65% water restriction with respect to water field capacity, 100% water, control condition.

To this end, transgenic and non-transformed plants were grown under water restraint conditions (65% water with respect to field capacity of 100% water in the soil). As can be seen in FIG. 18, under water stress conditions BBX21-overexpressing plants synthesize more chlorophyll with respect to WT plants. In turn, when water use efficiency (WUE) was measured, an improvement was observed in transgenic plants when compared to wild type plants (see FIG. 19).

Figure 20:
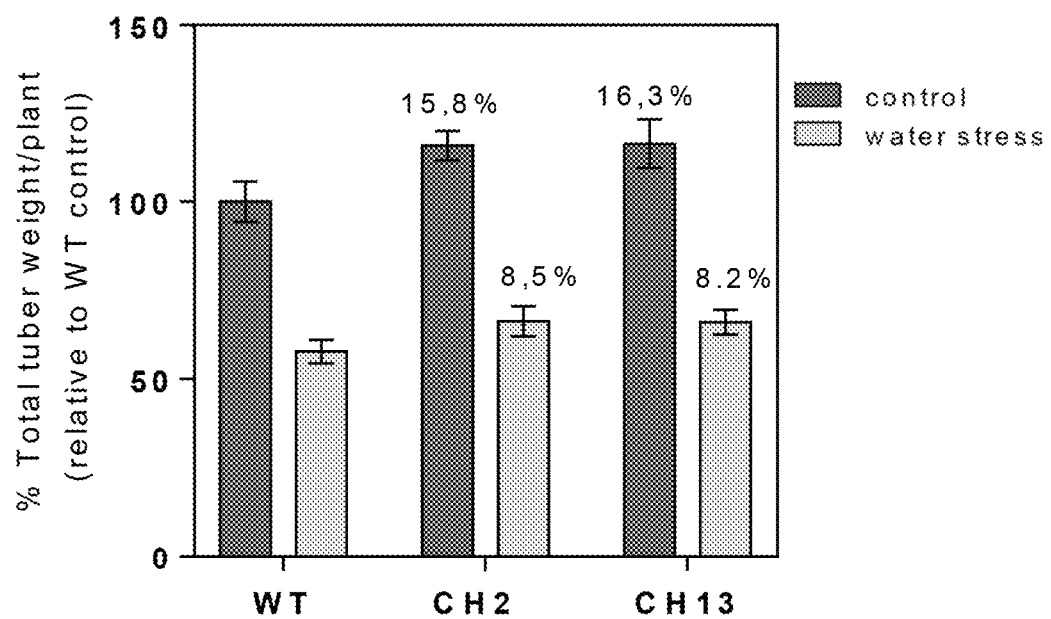
FIG. 20: Heterologous expression of AtBBX21 increases tuber yield in BBX21-overexpressing potatoes (CH2 and CH13) with respect to wild type Spunta plants cultivated under water stress, with 65% of water restriction with respect to the water field capacity of 100% (control).

Tuber production was also tested under this water shortage condition in the field. BBX21-overexpressing plants presented an increase of at least 8% by weight of tubers per plant with respect to control WT plants. Results are shown in FIG. 20.

In conclusion, water restraint improves the behavior of plants overexpressing the BBX21 event according to the present invention.

The invention claimed is:

1. A transgenic plant comprising a polynucleotide construct having the sequence of SEQ ID NO: 1, wherein said transgenic plant is obtained by *Agrobacterium*-mediated transformation of a wild-type plant cell,
   wherein the transgenic plant presents improved agronomic characteristics as compared to a wild-type, non-transformed plant,
   wherein the *Agrobacterium*-mediated transformation is effected on a plant cell from a plant selected from the group consisting of soybean, sorghum, potato, corn, tomato and barrel clover, and
   wherein said improved agronomic characteristics are selected from the group consisting of increased green and seed yield, reduced photoinhibition, improved water use efficiency, increased tuber production, increased chlorophyll production and improved photosynthetic rates, and a combination thereof.

2. The transgenic plant according to claim 1, wherein the transgenic plant is a transgenic potato plant.

3. A method for improving agronomical characteristics in crop plants, the method comprising:
   (i) providing an agronomical crop plant of interest, wherein the agronomical crop plant is selected from the group consisting of soybean, sorghum, potato, corn, tomato and barrel clover;
   (ii) transforming a cell of said agronomical crop plant with a polynucleotide construct having the sequence of SEQ ID NO: 1; and
   (iii) growing the transformed agronomical crop plant cell, wherein said improved agronomic characteristics are selected from the group consisting of increased green and seed yield, reduced photoinhibition, improved water use efficiency, increased tuber production, increased chlorophyll production and improved photosynthetic rates, and a combination thereof.

4. A method for obtaining a transgenic, stress-tolerant crop plant, the method comprising:
   (i) providing an agronomical crop plant of interest, wherein the agronomical crop plant is selected from the group consisting of soybean, sorghum, potato, corn, tomato and barrel clover;
   (ii) transforming a cell of said agronomical crop plant with a polynucleotide construct having the sequence of SEQ ID NO: 1; and
   (iii) growing the transformed agronomical crop plant cell, wherein the stress-tolerant crop plant is tolerant to a stress selected from a group consisting of water stress, high-irradiance stress, and a combination thereof.

5. The method according to claim 3, wherein the agronomical crop plant is a potato plant.

6. The method according to claim 4, wherein the agronomical crop plant is a potato plant.

* * * * *

SEQUENCE LISTING

<160> NUMBER OF SEQ ID NOS: 36

<210> SEQ ID NO 1
<211> LENGTH: 5175
<212> TYPE: DNA
<213> ORGANISM: Artificial Sequence
<220> FEATURE:
<223> OTHER INFORMATION: polynucleotide construct for X21 event

<400> SEQUENCE: 1

```
tgatcacagg cagcaacgct ctgtcatcgt tacaatcaac atgctaccct ccgcgagatc      60
atccgtgttt caaacccggc agcttagttg ccgttcttcc gaatagcatc ggtaacatga     120
gcaaagtctg ccgccttaca acggctctcc cgctgacgcc gtcccggact gatgggctgc     180
ctgtatcgag tggtgatttt gtgccgagct gccggtcggg gagctgttgg ctggctggtg     240
```

```
gcaggatata ttgtggtgta aacaaattga cgcttagaca acttaataac acattgcgga    300 cgttttaat  gtactgaatt aacgccgaat tgaattatca gcttgcatgc cggtcgatct    360
agtaacatag atgacaccgc gcgcgataat ttatcctagt ttgcgcgcta tattttgttt    420
tctatcgcgt attaaatgta taattgcggg actctaatca taaaaaccca tctcataaat    480
aacgtcatgc attacatgtt aattattaca tgcttaacgt aattcaacag aaattatatg    540
ataatcatcg caagaccggc aacaggattc aatcttaaga aactttattg ccaaatgttt    600
gaacgatctg cttgactcta gctagagtcc gaaccccaga gtcccgctca aagaactcg     660 tcaagaaggc gatagaaggc gatgcgctgc gaatcgggag cggcgatacc gtaaagcacg    720
aggaagcggt cagcccattc gccgccaagc tcttcagcaa tatcacgggt agccaacgct    780
atgtcctgat agcggtccgc cacacccagc cggccacagt cgatgaatcc agaaaagcgg    840
ccattttcca ccatgatatt cggcaagcag gcatcgccgt gggtcacgac gagatcctcg    900
ccgtcgggca tccgcgcctt gagcctggcg aacagttcgg ctggcgcgag ccctgatgc     960 tcttcgtcca gatcatcctg atcgacaaga ccggcttcca tccgagtacg tgctcgctcg   1020
atgcgatgtt tcgcttggtg gtcgaatggg caggtagccg gatcaagcgt atgcagccgc   1080
cgcattgcat cagccatgat ggatactttc tcggcaggag caaggtgaga tgacaggaga   1140
tcctgccccg gcacttcgcc caatagcagc cagtcccttc ccgcttcagt gacaacgtcg   1200
agcacagctg cgcaaggaac gcccgtcgtg gccagcacg  atagccgcgc tgcctcgtct   1260
tggagttcat tcagggcacc ggacaggtcg gtcttgacaa aaagaaccgg gcgcccctgc   1320
gctgacagcc ggaacacggc ggcatcagag cagccgattg tctgttgtgc ccagtcatag   1380
ccgaatagcc tctccaccca agcggccgga gaacctgcgt gcaatccatc ttgttcaatc   1440
atgcctcgat cgagttgaga gtgaatatga gactctaatt ggataccgag gggaatttat   1500
ggaacgtcag tggagcattt ttgacaagaa atatttgcta gctgatagtg accttaggcg   1560
acttttgaac gcgcaataat ggtttctgac gtatgtgctt agctcattaa actccagaaa   1620
cccgcggctg agtggctcct tcaacgttgc ggttctgtca gttccaaacg taaaacggct   1680
tgtcccgcgt catcggcggg ggtcataacg tgactccctt aattctcatg tatgataatt   1740
cgagctctcc catatggtcg actagagcca agctgatctc ctttgccccg gagatcacca   1800
tggacgactt tctctatctc tacgatctag gaagaaagtt cgacggagaa ggtgacgata   1860
ccatgttcac caccgataat gagaagatta gcctcttcaa tttcagaaag aatgctgacc   1920
cacagatggt tagagaggcc tacgcggcag gtctcatcaa gacgatctac ccgagtaata   1980
atctccagga gatcaaatac cttcccaaga aggttaaaga tgcagtcaaa agattcagga   2040
ctaactgcat caagaacaca gagaaagata tatttctcaa gatcagaagt actattccag   2100
tatggacgat tcaaggcttg cttcataaac caaggcaagt aatagagatt ggagtctcta   2160
agaaagtagt tcctactgaa tcaaaggcca tggagtcaaa aattcagatc gaggatctaa   2220
cagaactcgc cgtgaagact ggcgaacagt tcatacagag tcttttacga ctcaatgaca   2280
agaagaaaat cttcgtcaac atggtggagc acgacactct cgtctactcc aagaatatca   2340
aagatacagt ctcagaagac caagggcta  ttgagctttt caacaaaggg taatatcgg    2400 gaaacctcct cggattccat tgcccagcta tctgtcactt catcaaaagg acagtagaaa   2460
aggaaggtgg cacctacaaa tgccatcatt gcgataaagg aaaggctatc gttcaagatg   2520
cctctgccga cagtggtccc aaagatggac ccccacccac gaggagcatc gtggaaaaag   2580
aagacgttcc aaccacgtct tcaaagcaag tggattgatg tgatatctcc actgacgtaa   2640
```

```
gggatgacgc acaatcccac tatccttcgc aagacccttc ctctatataa ggaagttcat      2700
ttcatttgga gaggactccg gtattttttac aacaatacca caacaaaaca aacaacaaac      2760
aacattacaa tttactattc tagtcgacct gcaggcggcc gcactagtga tatcacaagt      2820
ttgtacaaaa aagctgaacg agaaacgtaa atgatataa atatcaatat attaaattag      2880
attttgcata aaaaacagac tacataaatac tgtaaaacac aacatatcca gtcactatga      2940
tgagttcaac tgtttcaaat ccccaaggaa tcctgcaacc aggctcattt ctgcttccag      3000
aatcagaatc tatgaaaaaa gaggaagcag agttagtttc tgtgtgttgg aatcaggatt      3060
caagttgttt tgcagctgga acgagtcatg gtttttcgtat atataactgt gaaccttttca      3120 aagaaacttt caggcgtgag ctaaaggacg gtggttttaa aatcgtagag atgcttttcc      3180
gtagcaatat actggcactt gttggtggtg gacctaactc tcagtatcct tcaagcaaag      3240
tactaatttg ggatgatcat cagagccgtt gcattagtga atttgcattt aggtctgaga      3300
ttcgtgcagt gaaattaaga agggatcgga ttgttgttgt tcttgaacat aagatttatg      3360
tttataactt tatggatctt agacttcttc atcagattga aactcaagct aatcctagag      3420
gattgtgttg cctttctcat cattctaata cgtctgtgtt ggcttgccct ggtctcaatc      3480
gaggagagat tcgtgttgaa catttcgggc ttaacatggt acaaatcata aatgctcatg      3540
attcaagtat tgcgtgtatg accttgacat tggatggttt gttgcttgca actgctagta      3600
caaagggaac tctgattaga atcttcaaca caatggatgg aactcgtttg caagaggtaa      3660
atatcagata ctggttttgct ttgatcactg tattacatta ctaacaattc aaaggtgttt      3720
ctttataggt acgaagagga gtcgacagag cagatatata tagcattgca ctttcaccaa      3780
atgtgcagtg gctggcggta tcaagtgaca aggggactgt tcacattttc tctcttagag      3840
ttagggttgt tggggaggat tcttattcca ctgaaaatgg agctctgttg acacaacaaa      3900
attattctaa ttctctgcaa ggccttgttt ctccaaccat tggtaccaat cccggttcgt      3960
cattgtcgtt tatgagaggt aaggaaaaat tctatgtagt agctctaagt ccaagagatt      4020
tattgactat gtagtagcta agtccaagag atttactccc ttcatagttg caggattgtt      4080
aagattatac atttttgtta acgttattct ttctcttgtt tattatctct tccatgaatg      4140
tagaaatggg aagaatggtg ttttttgaaat gctactttga agccttaaaa attcgttcgc      4200
tctttcttac ctaacatgta cactcttgtt gcaggtgttc taccaaagta tttcagctcg      4260
gaatggtcat atgcacagtt tcatgtatca gaagtcacac aattcttcgc agcatttggc      4320
agtaacaaca cggttgctat tatcggcatg gatggaaggt ataatcccaa ataagcccat      4380
tcactttgta tttccatcac actaccagga atctttaacc agagcaagta cactagttgt      4440
gcatctataa aaaccactct cagatctcgg cttagtgctt acttgtgttt tcttgtctca      4500
gtttctaccg atgcagcttt gatcccgtga acggaggaga gatggggcaa ctggaatata      4560
tccactttat gaagatggac aaccgcccgt gacatagtga ctggatatgt tgtgttttac      4620
agtattatgt agtctgtttt ttatgcaaaa tctaatttaa tatattgata tttatatcat      4680
tttacgtttc tcgttcagct ttcttgtaca aagtggtgat atcccgcggc catgctagag      4740
tccgcaaaaa tcaccagtct ctctctacaa atctatctct ctctattttt ctccagaata      4800
atgtgtgagt agttcccaga taagggaatt agggttctta tagggtttcg ctcatgtgtt      4860
gagcatataa gaaacccta gtatgtattt gtatttgtaa aatacttcta tcaataaaat      4920
ttctaattcc taaaaccaaa atccagtgac ctgcaggcat gcgacgtcgg gcccaagctt      4980
```

```
agcttgagct tggatcagat tgtcgtttcc cgccttcagt ttaaactatc agtgtttgac    5040
aggatatatt ggcgggtaaa cctaagagaa aagagcgttt attagaataa cggatattta    5100
aaagggcgtg aaaaggttta tccgttcgtc catttgtatg tgcatgccaa ccacagggtt    5160
cccctcggga tcaaa                                                     5175

<210> SEQ ID NO 2
<211> LENGTH: 51
<212> TYPE: DNA
<213> ORGANISM: Artificial Sequence
<220> FEATURE:
<223> OTHER INFORMATION: forward primer GatFor172

<400> SEQUENCE: 2
ggggacaagt ttgtacaaaa aagcaggctc catgaagatc aggtgcgacg t              51

<210> SEQ ID NO 3
<211> LENGTH: 50
<212> TYPE: DNA
<213> ORGANISM: Artificial Sequence
<220> FEATURE:
<223> OTHER INFORMATION: reverse primer GatRev_172

<400> SEQUENCE: 3
ggggaccact ttgtacaaga aagctgggtc ttaccagaaa gatctaaact                50

<210> SEQ ID NO 4
<211> LENGTH: 1653
<212> TYPE: DNA
<213> ORGANISM: Arabidopsis thaliana

<400> SEQUENCE: 4
atgagttcaa ctgtttcaaa tccccaagga atcctgcaac caggctcatt tctgcttcca      60
gaatcagaat ctatgaaaaa agaggaagca gagttagttt ctgtgtgttg gaatcaggat     120
tcaagttgtt ttgcagctgg aacgagtcat ggttttcgta tatataactg tgaacctttc     180
aaagaaactt tcaggcgtga gctaaaggac ggtggtttta aaatcgtaga gatgcttttc     240
cgtagcaata tactggcact tgttggtggt ggacctaact ctcagtatcc ttcaagcaaa     300
gtactaattt gggatgatca tcagagccgt tgcattagtg aatttgcatt taggtctgag     360
attcgtgcag tgaaattaag aagggatcgg attgttgttg ttcttgaaca taagatttat     420
gtttataact ttatggatct tagacttctt catcagattg aaactcaagc taatcctaga     480
ggattgtgtt gcctttctca tcattctaat acgtctgtgt tggcttgccc tggtctcaat     540
cgaggagaga ttcgtgttga acatttcggg cttaacatgg tacaaatcat aaatgctcat     600
gattcaagta ttgcgtgtat gaccttgaca ttggatggtt tgttgcttgc aactgctagt     660
acaaagggaa ctctgattag aatcttcaac acaatggatg gaactcgttt gcaagaggta     720
aatatcagat actggtttgc tttgatcact gtattacatt actaacaatt caaaggtgtt     780
tctttatagg tacgaagagg agtcgacaga gcagatatat atagcattgc actttcacca     840
aatgtgcagt ggctggcggt atcaagtgac aaggggactg ttcacatttt ctctcttaga     900 gttaggttg ttggggagga ttcttattcc actgaaaatg gagctctgtt gacacaacaa     960
aattattcta attctctgca aggccttgtt tctccaacca ttggtaccaa tcccggttcg    1020
tcattgtcgt ttatgagagg taaggaaaaa ttctatgtag tagctctaag tccaagagat    1080
ttattgacta tgtagtagct aagtccaaga gattactccc ttcatagttg caggattgt     1140 taagattata catttttgtt aacgttattc tttctcttgt ttattatctc ttccatgaat    1200
```

```
gtagaaatgg gaagaatggt gttttttgaaa tgctactttg aagccttaaa aattcgttcg    1260
ctctttctta cctaacatgt acactcttgt tgcaggtgtt ctaccaaagt atttcagctc    1320
ggaatggtca tatgcacagt ttcatgtatc agaagtcaca caattcttcg cagcatttgg    1380
cagtaacaac acggttgcta ttatcggcat ggatggaagg tataatccca aataagccca    1440
ttcactttgt atttccatca cactaccagg aatctttaac cagagcaagt acactagttg    1500
tgcatctata aaaaccactc tcagatctcg gcttagtgct tacttgtgtt ttcttgtctc    1560
agtttctacc gatgcagctt tgatcccgtg aacggaggag agatggggca actggaatat    1620
atccacttta tgaagatgga caaccgcccg tga                                 1653

<210> SEQ ID NO 5
<211> LENGTH: 19
<212> TYPE: DNA
<213> ORGANISM: Artificial Sequence
<220> FEATURE:
<223> OTHER INFORMATION: primer AtBBX21 sense

<400> SEQUENCE: 5
cgacatctgt caggataaa                                                  19

<210> SEQ ID NO 6
<211> LENGTH: 19
<212> TYPE: DNA
<213> ORGANISM: Artificial Sequence
<220> FEATURE:
<223> OTHER INFORMATION: primer AtBBX21 antisense

<400> SEQUENCE: 6
gttcgcagcg tggatcgat                                                  19

<210> SEQ ID NO 7
<211> LENGTH: 22
<212> TYPE: DNA
<213> ORGANISM: Artificial Sequence
<220> FEATURE:
<223> OTHER INFORMATION: primer TUB sense

<400> SEQUENCE: 7
aacctccatt caggagatgt tt                                              22

<210> SEQ ID NO 8
<211> LENGTH: 22
<212> TYPE: DNA
<213> ORGANISM: Artificial Sequence
<220> FEATURE:
<223> OTHER INFORMATION: primer TUB antisense

<400> SEQUENCE: 8
tctgctgtag catcctggta tt                                              22

<210> SEQ ID NO 9
<211> LENGTH: 20
<212> TYPE: DNA
<213> ORGANISM: Artificial Sequence
<220> FEATURE:
<223> OTHER INFORMATION: primer StLHCB1 sense

<400> SEQUENCE: 9
tcttggccat ctgggcttgc                                                 20

<210> SEQ ID NO 10
```

-continued

<210> SEQ ID NO 10
<211> LENGTH: 20
<212> TYPE: DNA
<213> ORGANISM: Artificial Sequence
<220> FEATURE:
<223> OTHER INFORMATION: primer StLHCB1 antisense

<400> SEQUENCE: 10
tgggtcaaag ctgccaccag                                       20

<210> SEQ ID NO 11
<211> LENGTH: 20
<212> TYPE: DNA
<213> ORGANISM: Artificial Sequence
<220> FEATURE:
<223> OTHER INFORMATION: primer StRCA sense

<400> SEQUENCE: 11
actgggcacc aaccagagaa                                       20

<210> SEQ ID NO 12
<211> LENGTH: 20
<212> TYPE: DNA
<213> ORGANISM: Artificial Sequence
<220> FEATURE:
<223> OTHER INFORMATION: primer StRCA antisense

<400> SEQUENCE: 12
agggaaggca tcgacaagcc                                       20

<210> SEQ ID NO 13
<211> LENGTH: 20
<212> TYPE: DNA
<213> ORGANISM: Artificial Sequence
<220> FEATURE:
<223> OTHER INFORMATION: primer StFTSZ1 sense

<400> SEQUENCE: 13
cagtctgctg ccgagaaccc                                       20

<210> SEQ ID NO 14
<211> LENGTH: 20
<212> TYPE: DNA
<213> ORGANISM: Artificial Sequence
<220> FEATURE:
<223> OTHER INFORMATION: primer StFTSZ1 antisense

<400> SEQUENCE: 14
gactcctccg ctgcctgttc                                       20

<210> SEQ ID NO 15
<211> LENGTH: 20
<212> TYPE: DNA
<213> ORGANISM: Artificial Sequence
<220> FEATURE:
<223> OTHER INFORMATION: primer AtF3H sense

<400> SEQUENCE: 15
aaggttgggt gaaagtgacg                                       20

<210> SEQ ID NO 16
<211> LENGTH: 20
<212> TYPE: DNA
<213> ORGANISM: Artificial Sequence
<220> FEATURE:
<223> OTHER INFORMATION: primer AtF3H antisense

<400> SEQUENCE: 16
tcagtgtgac gcttgagtcc 20

<210> SEQ ID NO 17
<211> LENGTH: 20
<212> TYPE: DNA
<213> ORGANISM: Artificial Sequence
<220> FEATURE:
<223> OTHER INFORMATION: primer AtCHI sense

<400> SEQUENCE: 17
cgggatcgct gtgatcgaga 20

<210> SEQ ID NO 18
<211> LENGTH: 20
<212> TYPE: DNA
<213> ORGANISM: Artificial Sequence
<220> FEATURE:
<223> OTHER INFORMATION: primer AtCHI antisense

<400> SEQUENCE: 18
gccaggtgac acaccgttct 20

<210> SEQ ID NO 19
<211> LENGTH: 20
<212> TYPE: DNA
<213> ORGANISM: Artificial Sequence
<220> FEATURE:
<223> OTHER INFORMATION: primer AtCHS sense

<400> SEQUENCE: 19
cggcgtcgac atgcctggtg 20

<210> SEQ ID NO 20
<211> LENGTH: 20
<212> TYPE: DNA
<213> ORGANISM: Artificial Sequence
<220> FEATURE:
<223> OTHER INFORMATION: primer AtCHS antisense

<400> SEQUENCE: 20
agtaccgccg gcgaagcaac 20

<210> SEQ ID NO 21
<211> LENGTH: 19
<212> TYPE: DNA
<213> ORGANISM: Artificial Sequence
<220> FEATURE:
<223> OTHER INFORMATION: primer StCHS sense

<400> SEQUENCE: 21
ctatggcaat atgtcaagt 19

<210> SEQ ID NO 22
<211> LENGTH: 18
<212> TYPE: DNA
<213> ORGANISM: Artificial Sequence
<220> FEATURE:
<223> OTHER INFORMATION: primer StCHS antisense

<400> SEQUENCE: 22
cttcacctgt agttccta 18

<210> SEQ ID NO 23
<211> LENGTH: 20
<212> TYPE: DNA

```
<213> ORGANISM: Artificial Sequence
<220> FEATURE:
<223> OTHER INFORMATION: primer StF3H sense

<400> SEQUENCE: 23
acattcggat cctggtggca                                              20

<210> SEQ ID NO 24
<211> LENGTH: 20
<212> TYPE: DNA
<213> ORGANISM: Artificial Sequence
<220> FEATURE:
<223> OTHER INFORMATION: primer StF3H antisense

<400> SEQUENCE: 24
gttgttgcgt cggacctgaa                                              20

<210> SEQ ID NO 25
<211> LENGTH: 20
<212> TYPE: DNA
<213> ORGANISM: Artificial Sequence
<220> FEATURE:
<223> OTHER INFORMATION: primer StCHI sense

<400> SEQUENCE: 25
tgcccttgac gggtaagcaa                                              20

<210> SEQ ID NO 26
<211> LENGTH: 20
<212> TYPE: DNA
<213> ORGANISM: Artificial Sequence
<220> FEATURE:
<223> OTHER INFORMATION: primer StCHI antisense

<400> SEQUENCE: 26
ggcaccaggt gggaaggttt                                              20

<210> SEQ ID NO 27
<211> LENGTH: 19
<212> TYPE: DNA
<213> ORGANISM: Artificial Sequence
<220> FEATURE:
<223> OTHER INFORMATION: primer StPAL1 sense

<400> SEQUENCE: 27
catctccaca atggcttgg                                               19

<210> SEQ ID NO 28
<211> LENGTH: 19
<212> TYPE: DNA
<213> ORGANISM: Artificial Sequence
<220> FEATURE:
<223> OTHER INFORMATION: primer StPAL1 antisense

<400> SEQUENCE: 28
ttggaagttg ccaccatgt                                               19

<210> SEQ ID NO 29
<211> LENGTH: 20
<212> TYPE: DNA
<213> ORGANISM: Artificial Sequence
<220> FEATURE:
<223> OTHER INFORMATION: primer AtRCA1 sense

<400> SEQUENCE: 29
tcgttgagag ccttggagtt                                              20
```

<210> SEQ ID NO 30
<211> LENGTH: 20
<212> TYPE: DNA
<213> ORGANISM: Artificial Sequence
<220> FEATURE:
<223> OTHER INFORMATION: primer AtRCA1 antisense

<400> SEQUENCE: 30
ctgaggtagg tctcggcaag                                           20

<210> SEQ ID NO 31
<211> LENGTH: 20
<212> TYPE: DNA
<213> ORGANISM: Artificial Sequence
<220> FEATURE:
<223> OTHER INFORMATION: primer ATFD1 sense

<400> SEQUENCE: 31
aagaggtcga atgcgaagaa                                           20

<210> SEQ ID NO 32
<211> LENGTH: 20
<212> TYPE: DNA
<213> ORGANISM: Artificial Sequence
<220> FEATURE:
<223> OTHER INFORMATION: primer ATFD1 antisense

<400> SEQUENCE: 32
gtcggataag ccacacaggt                                           20

<210> SEQ ID NO 33
<211> LENGTH: 20
<212> TYPE: DNA
<213> ORGANISM: Artificial Sequence
<220> FEATURE:
<223> OTHER INFORMATION: primer AtLHCA1 sense

<400> SEQUENCE: 33
cgcttatgag ctgtggcata                                           20

<210> SEQ ID NO 34
<211> LENGTH: 20
<212> TYPE: DNA
<213> ORGANISM: Artificial Sequence
<220> FEATURE:
<223> OTHER INFORMATION: primer AtLHCA1 antisense

<400> SEQUENCE: 34
cgctggaact tcttcaagtc                                           20

<210> SEQ ID NO 35
<211> LENGTH: 11317
<212> TYPE: DNA
<213> ORGANISM: Artificial Sequence
<220> FEATURE:
<223> OTHER INFORMATION: nucleotide sequence of plasmid pK2GW7

<400> SEQUENCE: 35
ttgtgtaggg cttattatgc acgcttaaaa ataataaaag cagacttgac ctgatagttt    60
ggctgtgagc aattatgtgc ttagtgcatc taatcgcttg agttaacgcc ggcgaagcgg   120
cgtcggcttg aacgaatttc tagctagaca ttatttgccg actaccttgg tgatctcgcc   180
tttcacgtag tggacaaatt cttccaactg atctgcgcgc gaggccaagc gatcttcttc   240

```
ttgtccaaga taagcctgtc tagcttcaag tatgacgggc tgatactggg ccggcaggcg    300
ctccattgcc cagtcggcag cgacatcctt cggcgcgatt ttgccggtta ctgcgctgta    360
ccaaatgcgg acaacgtaa gcactacatt tcgctcatcg ccagcccagt cgggcggcga    420 gttcctatagc gttaaggttt catttagcgc ctcaaataga tcctgttcag gaaccggatc    480
aaagagttcc tccgccgctg gacctaccaa ggcaacgcta tgttctcttg cttttgtcag    540
caagatagcc agatcaatgt cgatcgtggc tggctcgaag atacctgcaa gaatgtcatt    600
gcgctgccat tctccaaatt gcagttcgcg cttagctgga taacgccacg gaatgatgtc    660
gtcgtgcaca acaatggtga cttctacagc gcggagaatc tcgctctctc caggggaagc    720
cgaagtttcc aaaaggtcgt tgatcaaagc tcgccgcgtt gtttcatcaa gccttacggt    780
caccgtaacc agcaaatcaa tatcactgtg tggcttcagg ccgccatcca ctgcggagcc    840
gtacaaatgt acggccagca cgtcggttc gagatggcgc tcgatgacgc caactacctc    900
tgatagttga gtcgatactt cggcgatcac cgcttccccc atgatgttta actttgtttt    960
agggcgactg ccctgctgcg taacatcgtt gctgctccat aacatcaaac atcgacccac   1020
ggcgtaacgc gcttgctgct tggatgcccg aggcatagac tgtaccccaa aaaacatgt    1080 cataacaaga agccatgaaa accgccactg cgccgttacc accgctgcgt tcggtcaagg   1140
ttctggacca gttgcgtgac ggcagttacg ctacttgcat tacagcttac gaaccgaacg   1200
aggcttatgt ccactgggtt cgtgcccgaa ttgatcacag gcagcaacgc tctgtcatcg   1260
ttacaatcaa catgctaccc tccgcgagat catccgtgtt tcaaacccgg cagcttagtt   1320
gccgttcttc cgaatagcat cggtaacatg agcaaagtct gccgccttac aacggctctc   1380
ccgctgacgc cgtcccggac tgatgggctg cctgtatcga gtggtgattt tgtgccgagc   1440
tgccggtcgg ggagctgttg gctggctggt ggcaggatat attgtggtgt aaacaaattg   1500
acgcttagac aacttaataa cacattgcgg acgtttttaa tgtactgaat taacgccgaa   1560
ttgaattatc agcttgcatg ccggtcgatc tagtaacata gatgacaccg cgcgcgataa   1620
tttatcctag tttgcgcgct atattttgtt ttctatcgcg tattaaatgt ataattgcgg   1680
gactctaatc ataaaaaccc atctcataaa taacgtcatg cattacatgt taattattac   1740
atgcttaacg taattcaaca gaaattatat gataatcatc gcaagaccgg caacaggatt   1800
caatcttaag aaactttatt gccaaatgtt tgaacgatct gcttgactct agctagagtc   1860
cgaaccccag agtcccgctc agaagaactc gtcaagaagg cgatagaagg cgatgcgctg   1920
cgaatcggga gcggcgatac cgtaaagcac gaggaagcgg tcagcccatt cgccgccaag   1980
ctcttcagca atatcacggg tagccaacgc tatgtcctga tagcggtccg ccacacccag   2040
ccggccacag tcgatgaatc cagaaaagcg gccattttcc accatgatat tcggcaagca   2100
ggcatcgccg tgggtcacga cgagatcctc gccgtcgggc atccgcgcct tgagcctggc   2160
gaacagttcg gctggcgcga gcccctgatg ctcttcgtcc agatcatcct gatcgacaag   2220
accggcttcc atccgagtac gtgctcgctc gatgcgatgt ttcgcttggt ggtcgaatgg   2280
gcaggtagcc ggatcaagcg tatgcagccg ccgcattgca tcagccatga tggatacttt   2340
ctcggcagga gcaaggtgag atgacaggag atcctgcccc ggcacttcgc ccaatagcag   2400
ccagtccctt cccgcttcag tgacaacgtc gagcacagct gcgcaaggaa cgcccgtcgt   2460
ggccagccac gatagccgcg ctgcctcgtc ttggagttca ttcagggcac cggacaggtc   2520
ggtcttgaca aaaagaaccg ggcgcccctg cgctgacagc cggaacacgg cggcatcaga   2580
gcagccgatt gtctgttgtg cccagtcata gccgaatagc ctctccaccc aagcggccgg   2640
```

```
agaacctgcg tgcaatccat cttgttcaat catgcctcga tcgagttgag agtgaatatg   2700
agactctaat tggataccga ggggaattta tggaacgtca gtggagcatt tttgacaaga   2760
aatatttgct agctgatagt gaccttaggc gacttttgaa cgcgcaataa tggtttctga   2820
cgtatgtgct tagctcatta aactccagaa acccgcggct gagtggctcc ttcaacgttg   2880
cggttctgtc agttccaaac gtaaaacggc ttgtcccgcg tcatcggcgg gggtcataac   2940
gtgactccct taattctcat gtatgataat tcgagctctc ccatatggtc gactagagcc   3000
aagctgatct cctttgcccc ggagatcacc atggacgact ttctctatct ctacgatcta   3060
ggaagaaagt tcgacggaga aggtgacgat accatgttca ccaccgataa tgagaagatt   3120
agcctcttca atttcagaaa gaatgctgac ccacagatgg ttagagaggc ctacgcggca   3180
ggtctcatca agacgatcta cccgagtaat aatctccagg agatcaaata ccttcccaag   3240
aaggttaaag atgcagtcaa aagattcagg actaactgca tcaagaacac agagaaagat   3300
atatttctca agatcagaag tactattcca gtatggacga ttcaaggctt gcttcataaa   3360
ccaaggcaag taatagagat tggagtctct aagaaagtag ttcctactga atcaaaggcc   3420
atggagtcaa aaattcagat cgaggatcta acagaactcg ccgtgaagac tggcgaacag   3480
ttcatacaga gtcttttacg actcaatgac aagaagaaaa tcttcgtcaa catggtggag   3540
cacgacactc tcgtctactc caagaatatc aaagatacag tctcagaaga ccaagggct   3600 attgagactt tcaacaaag gtaatatcg ggaaacctcc tcggattcca ttgcccagct   3660
atctgtcact tcatcaaaag gacagtagaa aaggaaggtg gcacctacaa atgccatcat   3720
tgcgataaag gaaaggctat cgttcaagat gcctctgccg acagtggtcc caagatgga   3780 cccccaccca cgaggagcat cgtggaaaaa gaagacgttc caaccacgtc ttcaaagcaa   3840
gtggattgat gtgatatctc cactgacgta agggatgacg cacaatccca ctatccttcg   3900
caagaccctt cctctatata aggaagttca tttcatttgg agaggactcc ggtattttta   3960
caacaatacc acaacaaaac aaacaacaaa caacattaca atttactatt ctagtcgacc   4020
tgcaggcggc cgcactagtg atatcacaag tttgtacaaa aaagctgaac gagaaacgta   4080
aaatgatata aatatcaata tattaaatta gattttgcat aaaaaacaga ctacataata   4140
ctgtaaaaca caacatatcc agtcactatg atgagttcaa ctgtttcaaa tccccaagga   4200
atcctgcaac caggctcatt tctgcttcca gaatcagaat ctatgaaaaa agaggaagca   4260
gagttagttt ctgtgtgttg gaatcaggat tcaagttgtt ttgcagctgg aacgagtcat   4320
ggttttcgta tataactg tgaaccttc aaagaaactt tcaggcgtga gctaaaggac   4380
ggtggtttta aaatcgtaga gatgcttttc cgtagcaata tactggcact tgttggtggt   4440
ggacctaact ctcagtatcc ttcaagcaaa gtactaattt gggatgatca tcagagccgt   4500
tgcattagtg aatttgcatt taggtctgag attcgtgcag tgaaattaag aagggatcgg   4560
attgttgttg ttcttgaaca taagatttat gtttataact ttatggatct tagacttctt   4620
catcagattg aaactcaagc taatcctaga ggattgtgtt gcctttctca tcattctaat   4680
acgtctgtgt tggcttgccc tggtctcaat cgaggagaga ttcgtgttga acatttcggg   4740
cttaacatgg tacaaatcat aaatgctcat gattcaagta ttgcgtgtat gaccttgaca   4800
ttggatggtt tgttgcttgc aactgctagt acaaagggaa ctctgattag aatcttcaac   4860
acaatggatg gaactcgttt gcaagaggta aatatcagat actggtttgc tttgatcact   4920
gtattacatt actaacaatt caaaggtgtt tctttatagg tacgaagagg agtcgacaga   4980
```

```
gcagatatat atagcattgc actttcacca aatgtgcagt ggctggcggt atcaagtgac    5040
aaggggactg ttcacatttt ctctcttaga gttagggttg ttggggagga ttcttattcc    5100
actgaaaatg gagctctgtt gacacaacaa aattattcta attctctgca aggccttgtt    5160
tctccaacca ttggtaccaa tcccggttcg tcattgtcgt ttatgagagg taaggaaaaa    5220
ttctatgtag tagctctaag tccaagagat ttattgacta tgtagtagct aagtccaaga    5280
gatttactcc cttcatagtt gcaggattgt taagattata cattttgtt aacgttattc     5340 tttctcttgt ttattatctc ttccatgaat gtagaaatgg gaagaatggt gttttgaaa     5400 tgctactttg aagccttaaa aattcgttcg ctctttctta cctaacatgt acactcttgt    5460
tgcaggtgtt ctaccaaagt atttcagctc ggaatggtca tatgcacagt ttcatgtatc    5520
agaagtcaca caattcttcg cagcatttgg cagtaacaac acggttgcta ttatcggcat    5580
ggatggaagg tataatccca aataagccca ttcactttgt atttccatca cactaccagg    5640
aatctttaac cagagcaagt acactagttg tgcatctata aaaaccactc tcagatctcg    5700
gcttagtgct tacttgtgtt ttcttgtctc agtttctacc gatgcagctt tgatcccgtg    5760
aacggaggag agatggggca actggaatat atccactta tgaagatgga caaccgcccg      5820
tgacatagtg actggatatg ttgtgtttta cagtattatg tagtctgttt tttatgcaaa    5880
atctaattta atatattgat atttatatca ttttacgttt ctcgttcagc tttcttgtac    5940
aaagtggtga tatcccgcgg ccatgctaga gtccgcaaaa atcaccagtc tctctctaca    6000
aatctatctc tctctatttt tctccagaat aatgtgtgag tagttcccag ataagggaat    6060
tagggttctt atagggtttc gctcatgtgt tgagcatata agaaacccctt agtatgtatt    6120 tgtatttgta aaatacttct atcaataaaa tttctaattc ctaaaaccaa aatccagtga    6180
cctgcaggca tgcgacgtcg ggcccaagct tagcttgagc ttggatcaga ttgtcgtttc    6240
ccgccttcag tttaaactat cagtgtttga caggatatat tggcgggtaa acctaagaga    6300
aaagagcgtt tattagaata acggatattt aaaagggcgt gaaaaggttt atccgttcgt    6360
ccatttgtat gtgcatgcca accacagggt tcccctcggg atcaaagtac tttgatccaa    6420
cccctccgct gctatagtgc agtcggcttc tgacgttcag tgcagccgtc ttctgaaaac    6480
gacatgtcgc acaagtccta agttacgcga caggctgccg ccctgccctt tcctggcgt     6540 tttcttgtcg cgtgttttag tcgcataaag tagaatactt gcgactagaa ccggagacat    6600
tacgccatga acaagagcgc cgccgctggc ctgctgggct atgcccgcgt cagcaccgac    6660
gaccaggact tgaccaacca acgggccgaa ctgcacgcgg ccggctgcac caagctgttt    6720
tccgagaaga tcaccggcac caggcgcgac cgcccggagc tggccaggat gcttgaccac    6780
ctacgccctg gcgacgttgt gacagtgacc aggctagacc gcctggcccg cagcacccgc    6840
gacctactgg acattgccga gcgcatccag gaggccggcg cgggcctgcg tagcctggca    6900
gagccgtggg ccgacaccac cacgccggcc ggccgcatgg tgttgaccgt gttcgccggc    6960
attgccgagt tcgagcgttc cctaatcatc gaccgcaccc ggagcgggcg cgaggccgcc    7020
aaggcccgag gcgtgaagtt tggcccccgc cctaccctca ccccggcaca gatcgcgcac    7080
gcccgcgagc tgatcgacca ggaaggccgc accgtgaaag aggcggctgc actgcttggc    7140
gtgcatcgct cgaccctgta ccgcgcactt gagcgcagcg aggaagtgac gcccaccgag    7200
gccaggcggc gcggtgcctt ccgtgaggac gcattgaccg aggccgacgc cctggcggcc    7260
gccgagaatg aacgccaaga ggaacaagca tgaaaccgca ccaggacggc caggacgaac    7320
cgtttttcat taccgaagag atcgaggcgg agatgatcgc ggccgggtac gtgttcgagc    7380
```

```
cgcccgcgca cgtctcaacc gtgcggctgc atgaaatcct ggccggtttg tctgatgcca    7440
agctggcggc ctggccggcc agcttggccg ctgaagaaac cgagcgccgc cgtctaaaaa    7500
ggtgatgtgt atttgagtaa aacagcttgc gtcatgcggt cgctgcgtat atgatgcgat    7560
gagtaaataa acaaatacgc aaggggaacg catgaaggtt atcgctgtac ttaaccagaa    7620
aggcgggtca ggcaagacga ccatcgcaac ccatctagcc cgcgccctgc aactcgccgg    7680
ggccgatgtt ctgttagtcg attccgatcc ccagggcagt gcccgcgatt gggcggccgt    7740
gcgggaagat caaccgctaa ccgttgtcgg catcgaccgc ccgacgattg accgcgacgt    7800
gaaggccatc ggccggcgcg acttcgtagt gatcgacgga gcgccccagg cggcggactt    7860
ggctgtgtcc gcgatcaagg cagccgactt cgtgctgatt ccggtgcagc caagcccta    7920 cgacatatgg gccaccgccg acctggtgga gctggttaag cagcgcattg aggtcacgga    7980
tggaaggcta caagcggcct tgtcgtgtc gcggcgatc aaaggcacgc gcatcggcgg    8040
tgaggttgcc gaggcgctgg ccgggtacga gctgcccatt cttgagtccc gtatcacgca    8100
gcgcgtgagc tacccaggca ctgccgccgc cggcacaacc gttcttgaat cagaacccga    8160
gggcgacgct gcccgcgagg tccaggcgct ggccgctgaa attaaatcaa aactcatttg    8220
agttaatgag gtaaagagaa aatgagcaaa agcacaaaca cgctaagtgc cggccgtccg    8280
agcgcacgca gcagcaaggc tgcaacgttg gccagcctgg cagacacgcc agccatgaag    8340
cgggtcaact ttcagttgcc ggcggaggat cacaccaagc tgaagatgta cgcggtacgc    8400
caaggcaaga ccattaccga gctgctatct gaatacatcg cgcagctacc agagtaaatg    8460
agcaaatgaa taatgagta gatgaatttt agcggctaaa ggaggcggca tggaaaatca    8520
agaacaacca ggcaccgacg ccgtggaatg ccccatgtgt ggaggaacgg gcggttggcc    8580
aggcgtaagc ggctgggttg tctgccggcc ctgcaatggc actggaaccc ccaagcccga    8640
ggaatcggcg tgacggtcgc aaaccatccg gcccggtaca aatcggcgcg cgctgggtg    8700 atgacctggt ggagaagttg aaggccgcgc aggccgccca gcggcaacgc atcgaggcag    8760
aagcacgccc cggtgaatcg tggcaagcgg ccgctgatcg aatccgcaaa gaatcccggc    8820
aaccgccggc agccggtgcg ccgtcgatta ggaagccgcc caaggcgac gagcaaccag    8880 attttttcgt tccgatgctc tatgacgtgg gcacccgcga tagtcgcagc atcatggacg    8940
tggccgtttt ccgtctgtcg aagcgtgacc gacgagctgg cgaggtgatc cgctacgagc    9000
ttccagacgg gcacgtagag gtttccgcag ggccggccgg catggccagt gtgtgggatt    9060
acgacctggt actgatggcg gtttcccatc taaccgaatc catgaaccga taccgggaag    9120
ggaagggaga caagcccggc cgcgtgttcc gtccacacgt tgcggacgta ctcaagttct    9180
gccggcgagc cgatggcgga aagcagaaag acgacctggt agaaacctgc attcggttaa    9240
acaccacgca cgttgccatg cagcgtacga agaaggccaa gaacggccgc ctggtgacgg    9300
tatccgaggg tgaagccttg attagccgct acaagatcgt aaagagcgaa accgggcggc    9360
cggagtacat cgagatcgag ctagctgatt ggatgtaccg cgagatcaca gaaggcaaga    9420
acccggacgt gctgacggtt caccccgatt acttttttgat cgatcccggc atcggccgtt    9480
ttctctaccg cctggcacgc cgcgccgcag gcaaggcaga agccagatgg ttgttcaaga    9540
cgatctacga acgcagtggc agcgccggag agttcaagaa gttctgtttc accgtgcgca    9600
agctgatcgg gtcaaatgac ctgccggagt acgatttgaa ggaggaggcg gggcaggctg    9660
gcccgatcct agtcatgcgc taccgcaacc tgatcgaggg cgaagcatcc gccggttcct    9720
```

| | |
|---|---|
| aatgtacgga gcagatgcta gggcaaattg ccctagcagg ggaaaaaggt cgaaaaggtc | 9780 |
| tctttcctgt ggatagcacg tacattggga acccaaagcc gtacattggg aaccggaacc | 9840 |
| cgtacattgg gaacccaaag ccgtacattg ggaaccggtc acacatgtaa gtgactgata | 9900 |
| taaaagagaa aaaaggcgat ttttccgcct aaaactcttt aaaacttatt aaaactctta | 9960 |
| aaacccgcct ggcctgtgca taactgtctg gccagcgcac agccgaagag ctgcaaaaag | 10020 |
| cgcctaccct tcggtcgctg cgctccctac gccccgccgc ttcgcgtcgg cctatcgcgg | 10080 |
| ccgctggccg ctcaaaaatg gctggcctac ggccaggcaa tctaccaggg cgcggacaag | 10140 |
| ccgcgccgtc gccactcgac cgccggcgcc cacatcaagg caccctgcct cgcgcgtttc | 10200 |
| ggtgatgacg gtgaaaacct ctgacacatg cagctcccgg agacggtcac agcttgtctg | 10260 |
| taagcggatg ccgggagcag acaagcccgt cagggcgcgt cagcgggtgt tggcgggtgt | 10320 |
| cggggcgcag ccatgaccca gtcacgtagc gatagcggag tgtatactgg cttaactatg | 10380 |
| cggcatcaga gcagattgta ctgagagtgc accatatgcg gtgtgaaata ccgcacagat | 10440 |
| gcgtaaggag aaaataccgc atcaggcgct cttccgcttc ctcgctcact gactcgctgc | 10500 |
| gctcggtcgt tcggctgcgg cgagcggtat cagctcactc aaaggcggta atacggttat | 10560 |
| ccacagaatc aggggataac gcaggaaaga acatgtgagc aaaaggccag caaaaggcca | 10620 |
| ggaaccgtaa aaaggccgcg ttgctggcgt ttttccatag gctccgcccc cctgacgagc | 10680 |
| atcacaaaaa tcgacgctca agtcagaggt ggcgaaaccc gacaggacta taaagatacc | 10740 |
| aggcgtttcc ccctggaagc tccctcgtgc gctctcctgt tccgaccctg ccgcttaccg | 10800 |
| gatacctgtc cgcctttctc ccttcgggaa gcgtggcgct ttctcatagc tcacgctgta | 10860 |
| ggtatctcag ttcggtgtag gtcgttcgct ccaagctggg ctgtgtgcac gaaccccccg | 10920 |
| ttcagcccga ccgctgcgcc ttatccggta actatcgtct tgagtccaac ccggtaagac | 10980 |
| acgacttatc gccactggca gcagccactg gtaacaggat tagcagagcg aggtatgtag | 11040 |
| gcggtgctac agagttcttg aagtggtggc ctaactacgg ctacactaga aggacagtat | 11100 |
| ttggtatctg cgctctgctg aagccagtta ccttcggaaa aagagttggt agctcttgat | 11160 |
| ccggcaaaca aaccaccgct ggtagcgtgt gttttttttgt ttgcaagcag cagattacgc | 11220 |
| gcagaaaaaa aggatctcaa gaagatcctt tgatcttttc tacgggtct gacgctcagt | 11280 |
| ggaacgaaaa ctcacgttaa gggattttgg tcatgca | 11317 |

```
<210> SEQ ID NO 36
<211> LENGTH: 10723
<212> TYPE: DNA
<213> ORGANISM: Artificial Sequence
<220> FEATURE:
<223> OTHER INFORMATION: Vector comprising the construct for the X21
      event
<220> FEATURE:
<221> NAME/KEY: misc_feature
<222> LOCATION: (6383)..(6383)
<223> OTHER INFORMATION: n is a, c, g, or t

<400> SEQUENCE: 36
```

| | |
|---|---|
| attcgggcac gaacccagtg gacataagcc tcgttcggtt cgtaagctgt aatgcaagta | 60 |
| gcgtaactgc cgtcacgcaa ctggtccaga accttgaccg aacgcagcgg tggtaacggc | 120 |
| gcagtggcgg ttttcatggc ttcttgttat gacatgtttt tttggggtac agtctatgcc | 180 |
| tcgggcatcc aagcagcaag cgcgttacgc cgtgggtcga tgtttgatgt tatggagcag | 240 |
| caacgatgtt acgcagcagg gcagtcgccc taaaacaaag ttaaacatca tgggggaagc | 300 |

-continued

```
ggtgatcgcc gaagtatcga ctcaactatc agaggtagtt ggcgtcatcg agcgccatct      360
cgaaccgacg ttgctggccg tacatttgta cggctccgca gtggatggcg gcctgaagcc      420
acacagtgat attgatttgc tggttacggt gaccgtaagg cttgatgaaa caacgcggcg      480
agctttgatc aacgaccttt tggaaacttc ggcttcccct ggagagagcg agattctccg      540
cgctgtagaa gtcaccattg ttgtgcacga cgacatcatt ccgtggcgtt atccagctaa      600
gcgcgaactg caatttggag aatggcagcg caatgacatt cttgcaggta tcttcgagcc      660
agccacgatc gacattgatc tggctatctt gctgacaaaa gcaagagaac atagcgttgc      720
cttggtaggt ccagcggcgg aggaactctt tgatccggtt cctgaacagg atctatttga      780
ggcgctaaat gaaaccttaa cgctatggaa ctcgccgccc gactgggctg gcgatgagcg      840
aaatgtagtg cttacgttgt cccgcatttg gtacagcgca gtaaccggca aaatcgcgcc      900
gaaggatgtc gctgccgact gggcaatgga gcgcctgccg gcccagtatc agcccgtcat      960
acttgaagct agacaggctt atcttggaca agaagaagat cgcttggcct cgcgcgcaga     1020
tcagttggaa gaatttgtcc actacgtgaa aggcgagatc accaaggtag tcggcaaata     1080
atgtctagct agaaattcgt tcaagccgac gccgcttcgc cggcgttaac tcaagcgatt     1140
agatgcacta agcacataat tgctcacagc caaactatca ggtcaagtct gcttttatta     1200
tttttaagcg tgcataataa gccctacaca aattgggaga tatatcatgc atgaccaaaa     1260
tcccttaacg tgagttttcg ttccactgag cgtcagaccc cgtagaaaag atcaaaggat     1320
cttcttgaga tccttttttt ctgcgcgtaa tctgctgctt gcaaacaaaa aaaccaccgc     1380
taccagcggt ggtttgtttg ccggatcaag agctaccaac tcttttccg aaggtaactg      1440
gcttcagcag agcgcagata ccaaatactg tccttctagt gtagccgtag ttaggccacc     1500
acttcaagaa ctctgtagca ccgcctacat acctcgctct gctaatcctg ttaccagtgg     1560
ctgctgccag tggcgataag tcgtgtctta ccgggttgga ctcaagacga tagttaccgg     1620
ataaggcgca gcggtcgggc tgaacggggg gttcgtgcac acagcccagc ttggagcgaa     1680
cgacctacac cgaactgaga tacctacagc gtgagctatg agaaagcgcc acgcttcccg     1740
aagggagaaa ggcggacagg tatccggtaa gcggcagggt cggaacagga gagcgcacga     1800
gggagcttcc agggggaaac gcctggtatc tttatagtcc tgtcgggttt cgccacctct     1860
gacttgagcg tcgatttttg tgatgctcgt caggggggcg gagcctatgg aaaaacgcca     1920
gcaacgcggc cttttacgg ttcctggcct tttgctggcc ttttgctcac atgttctttc      1980
ctgcgttatc ccctgattct gtggataacc gtattaccgc ctttgagtga gctgataccg     2040
ctcgccgcag ccgaacgacc gagcgcagcg agtcagtgag cgaggaagcg gaagagcgcc     2100
tgatgcggta ttttctcctt acgcatctgt gcggtatttc acaccgcata tggtgcactc     2160
tcagtacaat ctgctctgat gccgcatagt taagccagta tacactccgc tatcgctacg     2220
tgactgggtc atggctgcgc cccgacaccc gccaacaccc gctgacgcgc cctgacgggc     2280
ttgtctgctc ccggcatccg cttacagaca agctgtgacc gtctccggga gctgcatgtg     2340
tcagaggttt tcaccgtcat caccgaaacg cgcgaggcag ggtgccttga tgtgggcgcc     2400
ggcggtcgag tggcgacggc gcggcttgtc cgcgccctgg tagattgcct ggccgtaggc     2460
cagccatttt tgagcggcca gcggccgcga taggccgacg cgaagcggcg gggcgtaggg     2520
agcgcagcga ccgaagggta ggcgcttttt gcagctcttc ggctgtgcgc tggccagaca     2580
gttatgcaca ggccaggcgg gttttaagag ttttaataag ttttaaagag ttttaggcgg     2640
aaaaatcgcc ttttttctct tttatatcag tcacttacat gtgtgaccgg ttcccaatgt     2700
```

```
acggctttgg gttcccaatg tacgggttcc ggttcccaat gtacggcttt gggttcccaa    2760
tgtacgtgct atccacagga aagagacctt ttcgaccttt ttcccctgct agggcaattt    2820
gccctagcat ctgctccgta cattaggaac cggcggatgc ttcgccctcg atcaggttgc    2880
ggtagcgcat gactaggatc gggccagcct gccccgcctc ctccttcaaa tcgtactccg    2940
gcaggtcatt tgacccgatc agcttgcgca cggtgaaaca gaacttcttg aactctccgg    3000
cgctgccact gcgttcgtag atcgtcttga acaaccatct ggcttctgcc ttgcctgcgg    3060
cgcggcgtgc caggcggtag agaaaacggc cgatgccggg atcgatcaaa agtaatcgg    3120 ggtgaaccgt cagcacgtcc gggttcttgc cttctgtgat ctcgcggtac atccaatcag    3180
ctagctcgat ctcgatgtac tccggccgcc cggtttcgct ctttacgatc ttgtagcggc    3240
taatcaaggc ttcaccctcg ataccgtca ccaggcggcc gttcttggcc ttcttcgtac    3300
gctgcatggc aacgtgcgtg gtgtttaacc gaatgcaggt ttctaccagg tcgtctttct    3360
gctttccgcc atcggctcgc cggcagaact gagtacgtc cgcaacgtgt ggacggaaca    3420
cgcggccggg cttgtctccc ttcccttccc ggtatcggtt catggattcg gttagatggg    3480
aaaccgccat cagtaccagg tcgtaatccc acacactggc catgccggcc ggccctgcgg    3540
aaacctctac gtgcccgtct ggaagctcgt agcggatcac ctcgccagct cgtcggtcac    3600
gcttcgacag acgaaaaacg ccacgtcca tgatgctgcg actatcgcgg gtgcccacgt    3660
catagagcat cggaacgaaa aaatctggtt gctcgtcgcc cttgggcggc ttcctaatcg    3720
acggcgcacc ggctgccggc ggttgccggg attctttgcg gattcgatca gcggccgctt    3780
gccacgattc accggggcgt gcttctgcct cgatgcgttg ccgctgggcg gcctgcgcgg    3840
ccttcaactt ctccaccagg tcatcaccca gcgccgcgcc gatttgtacc gggccggatg    3900
gtttgcgacc gtcacgccga ttcctcgggc ttggggttc cagtgccatt gcagggccgg    3960
cagacaaccc agccgcttac gcctggccaa ccgcccgttc ctccacacat ggggcattcc    4020
acggcgtcgg tgcctggttg ttcttgattt tccatgccgc ctcctttagc cgctaaaatt    4080
catctactca tttattcatt tgctcattta ctctggtagc tgcgcgatgt attcagatag    4140
cagctcggta atggtcttgc cttggcgtac cgcgtacatc ttcagcttgg tgtgatcctc    4200
cgccggcaac tgaaagttga cccgcttcat ggctggcgtg tctgccaggc tggccaacgt    4260
tgcagccttg ctgctgcgtg cgctcggacg gccggcactt agcgtgtttg tgcttttgct    4320 catttctct ttacctcatt aactcaaatg agttttgatt taatttcagc ggccagcgcc    4380
tggacctcgc gggcagcgtc gccctcgggt tctgattcaa gaacggttgt gccggcggcg    4440
gcagtgcctg ggtagctcac gcgctgcgtg atacgggact caagaatggg cagctcgtac    4500
ccggccagcg cctcggcaac ctcaccgccg atgcgcgtgc ctttgatcgc ccgcgacacg    4560
acaaaggccg cttgtagcct tccatccgtg acctcaatgc gctgcttaac cagctccacc    4620
aggtcggcgg tggcccatat gtcgtaaggg cttggctgca ccggaatcag cacgaagtcg    4680
gctgccttga tcgcggacac agccaagtcc gccgcctggg gcgctccgtc gatcactacg    4740
aagtcgcgcc ggccgatggc cttcacgtcg cggtcaatcg tcgggcggtc gatgccgaca    4800
acggttagcg gttgatcttc ccgcacggcc gcccaatcgc gggcactgcc ctggggatcg    4860
gaatcgacta acagaacatc ggccccggcg agttgcaggg cgcgggctag atgggttgcg    4920
atggtcgtct tgcctgaccc gccttttctgg ttaagtacag cgataaccct catgcgttcc    4980
ccttgcgtat ttgtttattt actcatcgca tcatatacgc agcgaccgca tgacgcaagc    5040
```

```
tgttttactc aaatacacat cacctttta gacggcggcg ctcggtttct tcagcggcca    5100
agctggccgg ccaggccgcc agcttggcat cagacaaacc ggccaggatt tcatgcagcc    5160
gcacggttga gacgtgcgcg ggcggctcga acacgtaccc ggccgcgatc atctccgcct    5220
cgatctcttc ggtaatgaaa aacgttcgt cctggccgtc ctggtgcggt ttcatgcttg    5280
ttcctcttgg cgttcattct cggcggccgc cagggcgtcg gcctcggtca atgcgtcctc    5340
acggaaggca ccgcgccgcc tggcctcggt gggcgtcact tcctcgctgc gctcaagtgc    5400
gcggtacagg gtcgagcgat gcacgccaag cagtgcagcc gcctctttca cggtgcggcc    5460
ttcctggtcg atcagctcgc gggcgtgcgc gatctgtgcc ggggtgaggg tagggcgggg    5520
gccaaacttc acgcctcggg ccttggcggc ctcgcgcccg ctccgggtgc ggtcgatgat    5580
tagggaacgc tcgaactcgg caatgccggc gaacacggtc aacaccatgc ggccggccgg    5640
cgtggtggtg tcggcccacg gctctgccag gctacgcagg cccgcgccgg cctcctggat    5700
gcgctcggca atgtccagta ggtcgcgggt gctgcgggcc aggcggtcta gcctggtcac    5760
tgtcacaacg tcgccagggc gtaggtggtc aagcatcctg gccagctccg gcggtcgcg    5820
cctggtgccg gtgatcttct cggaaaacag cttggtgcag ccggccgcgt gcagttcggc    5880
ccgttggttg gtcaagtcct ggtcgtcggt gctgacgcgg gcatagccca gcaggccagc    5940
ggcggcgctc ttgttcatgg cgtaatgtct ccggttctag tcgcaagtat tctactttat    6000
gcgactaaaa cacgcgacaa gaaaacgcca ggaaaagggc agggcggcag cctgtcgcgt    6060
aacttaggac ttgtgcgaca tgtcgttttc agaagacggc tgcactgaac gtcagaagcc    6120
gactgcacta tagcagcgga ggggttggat caaagtactt tgatcccgag gggaaccctg    6180
tggttggcat gcacatacaa atggacgaac ggataaacct tttcacgccc ttttaaatat    6240
ccgttattct aataaacgct cttttctctt aggtttaccc gccaatatat cctgtcaaac    6300
actgatagtt taaactgaag gcgggaaacg acaatctgat ccaagctcaa gctaagcttg    6360
agctctccca tatggtcgag atntcctttg ccccggagat caccatggac gactttctct    6420
atctctacga tctaggaaga aagttcgacg gagaaggtga cgataccatg ttcaccaccg    6480
ataatgagaa gattagcctc ttcaatttca gaaagaatgc tgacccacag atggttagag    6540
aggcctacgc ggcaggtctc atcaagacga tctacccgag taataatctc caggagatca    6600
aataccttcc caagaaggtt aaagatgcag tcaaaagatt caggactaac tgcatcaaga    6660
acacagagaa agatatattt ctcaagatca gaagtactat tccagtatgg acgattcaag    6720
gcttgcttca taaccaagg caagtaatag agattggagt ctctaagaaa gtagttccta    6780
ctgaatcaaa ggccatggag tcaaaaattc agatcgagga tctaacagaa ctcgccgtga    6840
agactggcga acagttcata cagagtcttt tacgactcaa tgacaagaag aaaatcttcg    6900
tcaacatggt ggagcacgac actctcgtct actccaagaa tatcaaagat acagtctcag    6960
aagaccaaag ggctattgag acttttcaac aaagggtaat atcgggaaac ctcctcggat    7020
tccattgccc agctatctgt cacttcatca aaaggacagt agaaaggaa ggtggcacct    7080
acaaatgcca tcattgcgat aaaggaaagg ctatcgttca agatgcctct gccgacagtg    7140
gtcccaaaga tggaccccca cccacgagga gcatcgtgga aaaagaagac gttccaacca    7200
cgtcttcaaa gcaagtggat tgatgtgata tctccactga cgtaagggat gacgcacaat    7260
cccactatcc ttcgcaagac ccttcctcta tataaggaag ttcatttcat ttggagagga    7320
ctgcaggacg atccgtattt ttacaacaat taccacaaca aaacaaacaa caacaacat    7380
tacaatttac tattctagtc gacctgcagg cggccgcact agtgatatca caagtttgta    7440
```

```
caaaaaagct gaacgagaaa cgtaaaatga tataaatatc aatatattaa attagatttt    7500
gcataaaaaa cagactacat aatactgtaa aacacaacat atccagtcac tatggcggcc    7560
gcattaggca ccccaggctc catgaagatc aggtgcgacg tctgcgataa agaagaagcg    7620
tcggtgtttt gcacggccga cgaagcatct ctctgcggcg gctgcgacca ccaagtccac    7680
cacgctaaca aactcgcctc taaacatctc cgtttctctc tcctttatcc ttcttcttcc    7740
aacacctcct ctcctctctg cgacatcgtg caggtctctt tctaacttcg gacatgagtt    7800
ttgttgtctt aattcaatcg tttttgccga tcaagaatct gaaacttttt ctttttattg    7860
aactctagga taaaaagct ctgttgttct gtcaacaaga tagagctatt ttatgcaaag     7920
attgcgattc atcgatccac gctgcgaacg aacacacaaa gaaacacgat aggtttcttc    7980
ttacaggggt taagctctct gcaacatcgt ctgtttacaa acctacttcg aaatcttctt    8040
cttcttcttc aagcaaccaa gatttctctg tccctggatc atcaatctct aatcctcctc    8100
ctctcaagaa acctctctca gctcctcctc agagcaacaa gatccaaccc ttttcgaaga    8160
tcaacggcgg tgatgcgtcg gtgaatcagt ggggatccac aagcacgatt tctgagtatt    8220
tgatggatac gttacctggt tggcacgttg aggatttcct cgattcctct cttcctactt    8280
atggtttctc taaggtttgt tcttatctct ttaatcaaga aagatccaag tttagttgat    8340
ttcaagattt gacaatgacc cttagtagat tgaatttttt tttcctctgt ttacgtaata    8400
tcatatcatt ttagatctaa tgaggtatta atgtattata aaggtaacaa actttataga    8460
tgtggataga tctttttact atattgggta tttgtgtaaa atttctgaaa aagagttgtt    8520
ggttatcttt tgtgtgattg cagagtggtg atgatgatgg agtgttacca tatatggaac    8580
cagaagatga caacaacact aagagaaaca acaacaacaa caacaacaac aacaacaata    8640
cagtgtcact tccatctaag aatttaggga tttgggtccc tcagattcca caaactcttc    8700
cttcttcata cccaaatcaa tacttttctc aagacaacaa catacagttt gggatgtaca    8760
acaaagaaac atcaccagaa gtagtgtctt ttgctccaat acaaaacatg aaacaacaag    8820
gacagaacaa caagagatgg tatgatgatg gtggcttcac tgtcccacag atcactcctc    8880
ctcctctttc ttctaataaa aagtttagat cttttctggta agaccacgtt tctcgttcag    8940
ctttcttgta caaagtggtg atatcccgcg gccatgctag agtccgcaaa atcaccagt    9000 ctctctctac aaatctatct ctctctattt ttctccagaa taatgtgtga gtagttccca    9060
gataagggaa ttagggttct tatagggttt cgctcatgtg ttgagcatat aagaaaccct    9120
tagtatgtat ttgtatttgt aaaatacttc tatcaataaa atttctaatt cctaaaacca    9180
aaatccagtg acctgcaggc atgcgacgtc gggccctcta gaggatcccc gggtaccgcg    9240
aattatcata catgagaatt aagggagtca cgttatgacc cccgccgatg acgcgggaca    9300
agccgtttta cgtttggaac tgacagaacc gcaacgttga aggagccact cagccgggtt    9360
tctggagttt aatgagctaa gcacatacgt cagaaaccat tattgcgcgt tcaaagtcg    9420 cctaaggtca ctatcagcta gcaaatattt cttgtcaaaa atgctccact gacgttccat    9480
aaattcccct cggtatccaa ttagagtctc atattcactc tcaactcgat cgaggggat    9540 ctaccatgag cccagaacga cgcccggccg acatccgccg tgccaccgag gcggacatgc    9600
cggcggtctg caccatcgtc aaccactaca tccagacaag cacggtcaac ttccgtaccg    9660
agccgcagga accgcaggag tggacggacg acctcgtccg tctgcgggag cgctatccct    9720
ggctcgtcgc cgaggtggac ggcgaggtcg ccggcatcgc ctacgcgggt ccctggaagg    9780
```

```
cacgcaacgc ctacgactgg acggccgagt cgaccgtgta cgtctccccc cgccaccagc    9840
ggacgggact gggctccacg ctctacaccc acctgctgaa gtccctggag gcacagggct    9900
tcaagagcgt ggtcgctgtc atcgggctgc ccaacgaccc gagcgtgcgc atgcacgagg    9960
cgctcggata tgccccccgc ggcatgctgc gggcggccgg cttcaagcac gggaactggc   10020
atgacgtggg tttctggcag ctggacttca gcctgccggt gccgcccgt ccggtcctgc   10080 ccgtcaccga aatctgatga cccctagagt caagcagatc gttcaaacat ttggcaataa   10140
agtttcttaa gattgaatcc tgttgccggt cttgcgatga ttatcatata atttctgttg   10200
aattacgtta agcatgtaat aattaacatg taatgcatga cgttatttat gagatgggtt   10260
ttttgattag agtcccgcaa ttatacattt aatacgcgat agaaaacaaa atatagcgcg   10320
caaactagga taaattatcg cgcgcggtgt catctatgtt actagatcga ccggcatgca   10380
agctgataat tcaattcggc gttaattcag tacattaaaa acgtccgcaa tgtgttatta   10440
agttgtctaa gcgtcaattt gtttacacca caatatatcc tgccaccagc cagccaacag   10500
ctccccgacc ggcagctcgg cacaaaatca ccactcgata caggcagccc atcagtccgg   10560
gacggcgtca gcgggagagc cgttgtaagg cggcagactt tgctcatgtt accgatgcta   10620
ttcggaagaa cggcaactaa gctgccgggt ttgaaacacg gatgatctcg cggagggtag   10680
catgttgatt gtaacgatga cagagcgttg ctgcctgtga tca                    10723
```